(12) United States Patent
Grabbert et al.

(10) Patent No.: US 10,989,684 B2
(45) Date of Patent: Apr. 27, 2021

(54) BIOSENSOR, PROCESS FOR ITS PREPARATION AND METHOD FOR DETECTING AN ANALYTE USING THE BIOSENSOR

(71) Applicant: FRAUNHOFER-GESELLSCHAFT ZUR FOERDERUNG DER ANGEWANDTEN FORSCHUNG E.V., Munich (DE)

(72) Inventors: Niels Grabbert, Berlin (DE); Vera Meyer, Berlin (DE); Klaus-Dieter Lang, Berlin (DE); Markus Fiedler, Berlin (DE)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 62 days.

(21) Appl. No.: 16/301,104

(22) PCT Filed: May 12, 2017

(86) PCT No.: PCT/EP2017/061479
§ 371 (c)(1),
(2) Date: Nov. 13, 2018

(87) PCT Pub. No.: WO2017/194746
PCT Pub. Date: Nov. 16, 2017

(65) Prior Publication Data
US 2019/0187090 A1    Jun. 20, 2019

(30) Foreign Application Priority Data

May 13, 2016   (DE) .................... 10 2016 108 979.6

(51) Int. Cl.
*G01N 27/327*   (2006.01)
*G01N 27/30*    (2006.01)
(Continued)

(52) U.S. Cl.
CPC ......... *G01N 27/3278* (2013.01); *G01N 27/00* (2013.01); *G01N 27/308* (2013.01); *G01N 27/4146* (2013.01); *G01N 33/5438* (2013.01)

(58) Field of Classification Search
CPC .... G01N 27/026; G01N 27/30; G01N 27/308; G01N 27/327; G01N 27/3271; G01N 27/3275; G01N 27/3276; G01N 27/3278
See application file for complete search history.

(56) References Cited

U.S. PATENT DOCUMENTS

2013/0313523 A1   11/2013  Yun et al.

FOREIGN PATENT DOCUMENTS

KR   1020160004421 A   1/2016

OTHER PUBLICATIONS

NanoInnova webpage listing Products: Chemically Modified Graphene Oxide, downloaed from https://www.nanoinnova.com/products/chemically-modified-go on Jul. 10, 2020 (Year: 2020).*

(Continued)

*Primary Examiner* — Alexander S Noguerola
(74) *Attorney, Agent, or Firm* — Laurence A. Greenberg; Werner H. Sterner; Ralph E. Locher

(57) ABSTRACT

A biosensor has the following components: a sensor base with an insulating substrate and at least one electrically conductive working electrode arranged thereon, in particular formed from separately controllable interdigital electrodes, reduced graphene applied to at least one working electrode, a spacer covalently bound to the reduced graphene, and an antibody fragment Fab covalently bound to the spacer. There is also described a process for producing the biosensor, a biochip equipped with the sensor and a method of detecting an analyte using the biosensor/biochip.

14 Claims, 13 Drawing Sheets

(51) Int. Cl.
  G01N 27/414    (2006.01)
  G01N 33/543    (2006.01)
  G01N 27/00     (2006.01)

(56) References Cited

OTHER PUBLICATIONS

Supplementary Information (four pages) for Wu et al, "Simultaneous electrochecmial detection of cervical cancer markers using reduced graphene oxide-tetraethylene pentamine as elecrode materials and distninguishable redox probes as labels," Biosensors and Bioelectronics 54 (2014) (Year: 2014).*

Roy et al., "Graphene oxide for electrochemical sensing applications," J. Mater. Chem., 2011, 21, 14725 (Year: 2011).*

Huntsman, "Ethyleneamines—A Global Profile of Products and Services", 2007, pp. 1-76, found on the Internet http://www.huntsman.com/performance_products.

Sigma-Aldrich, "Product Specification for Tetraethylenepentamine—technical grade", Jun. 21, 2010, found on the Internet https://www.sigmaaldrich.com/catalog/product/aldrich/t11509?lang=en&region=NL.

Sigma-Aldrich, "Tetraethylene pentamine", Oct. 22, 2019, found on the Internet https://www.sigmaaldrich.com/catalog/product/mm/814713?lang=en&region=NL.

Xiaoyue Zhang, et al: "Ultrasensitive nonenzymatic immunosensor based on bimetallic gold-silver nanoclusters synthesized by simple mortar grinding route". Sensors and Actuators B: Chemical: International Journal Devoted to Research and Development of Physical and Chemical Transducers, vol. 194, 2014, pp. 64-70.

Dan Wu, et al.: "Simultaneous electrochemical detection of cervical cancer markers using reduced graphene oxide-tetraethylene pentamine as electrode materials and distinguishable redox probes as labels". Biosensors and Bioelectronics, vol. 54, Apr. 1, 2014 (Apr. 1, 2014), pp. 634-639, XP055389694, NL.

Kai Yang, et al.: "Preparation and functionalization of graphene nanocomposites for biomedical applications". Nature Protocols, vol. 8, No. 12, Nov. 7, 2013 (Nov. 7, 2013), pp. 2392-2403, XP055295539, GB ISSN: 1754-2189, DOI:10.1038jnprot.2013.146.

Jana Vlachova, et al.: "Utilization of graphene oxide electrophoretic deposition for construction of electrochemical sensors and biosensors". Journal of Metallomics and Nanotechnologies, vol. 3, Jan. 1, 2015 (Jan. 1, 2015), pp. 57-63, XP055390412.

Kim Truc Nguyen, et al.: "Graphene and Graphene Derrivatives in Biosensing, Imaging, Therapeutics, and Genetic Engineering". Rev. Cell Biol. Mol. Medicine, vol. 1, No. 1, Jan. 1, 2015 (Jan. 1, 2015), pp. 386-420, XP055389819, the whole document.

Lonkar Sunil, P., et al.: "Recent advances in chemical modifications of graphene". Nano Research, Tsinghua University Press, CN, vol . 8, No. 4, Nov. 28, 2014 (Nov. 28, 2014), pp. 1039-1874.

Numan Celik, et al.: "Graphene-based biosensors: methods, analysis and future perspectives". IET Circuits Devices and Syst., The Institution of Engineering and Technology, GB, vol . 9, No. 6, Nov. 1, 2815 (Nov. 1, 2015), pp. 434-445.

Wojtoniszak, Malgorzata, et al.: "Synthesis, dispersion, and cytocompatibility of graphene oxide and reduced graphene oxide". Colloids and Surfaces B: Biointerfaces, journal homepage: www.elsevier.com/locate/colsurfb.

Zagorodko,Oleksandr, et al.: " Highly Sensitive Detection of DNA Hybridization on Commercialized Graphene-Coated Surface Plasmon Resonance Interfaces". Institut de Recherche Interdisciplinaire, USR 3078 CNRS, Université Lille 1, Parc de la Haute Borne, 50 Avenue de Halley, 6 BP 70478, 59658 Villeneuve d'Ascq, France.

Zagorodko, Oleksandr, et al.: Highly sensitive detection of DNA hybridization on commercialized graphene coated surface plasmon resonance interfaces. Anal. Chen., Just accepted Manuscript DOI: 10.1021/ac502705n, Publication Date (Web): Oct. 23, 2014, http://pubs.acs.org on Nov. 2, 2014.

Jevsevar, Simona, et al: "PEGylation of Antibody Fragments for Half-Life Extension". Gabriele Proetzel and Hilmar Ebersbach (eds.), Antibody Methods and Protocols, Methods in Molecular Biology, vol. 901, DOI 10.1007/978-1-61779-931-0_15, © Springer Science+Business Media, LLC 2012.

Huang, Ke-Jing, et al.: "Novel electrochemical sensor based on functionalized graphene for simultaneous determination of adenine and guanine in DNA". Contents lists available at ScienceDirect, Colloids and Surfaces B: Biointerfaces, journal homepage: www.elsevier.com/locate/colsurfb.

Yanez-Sedeno, P., et al.: "Electrochemical immunosensor for sensitive determination of the anorexigen peptide YY at grafted reduced graphene oxide electrode platforms". Department of Analytical Chemistry, Faculty of Chemistry, University Complutense of Madrid, 28040-Madrid, Spain. This journal is the Royal Society of Chemistry 2015, Analyst, 2015.

Zhao, Y., et al. : "Rapidly accomplished femtomole soluble CD 40 ligand detection in human serum: a "green" homobifunctional agent coupled with reduced graphene oxide-tetraethylene pentamine as platform". Institute of Life Science and School of Public Health, Chongqing Medical University, Box 174# No. 1 Yixueyuan Road, Yuzhong District, Chongqing 400016, P.R. China.

* cited by examiner

BIOSENSOR, PROCESS FOR ITS PREPARATION AND METHOD FOR DETECTING AN ANALYTE USING THE BIOSENSOR

FIELD OF THE INVENTION

The present invention relates to a biosensor, a method for producing the same, a chip carrying the biosensor, and a method for detecting an analyte (an antigen or biomarker) to be detected.

STATE OF THE ART

Graphene is an ultrathin layer made up of carbon atoms bound to each other in a honeycomb pattern. Due to its excellent electrical ability in combination with a high chemical and mechanical stability, it offers far reaching applications. By means of chemical functionalization, it is not only possible to produce stable graphite suspensions, but also to control its interaction with other materials, which is of great importance for the realization of products. Reduced graphene oxide (rGO) is mainly used for these purposes (Wojtoniszak, M. et al. 2012), "Synthesis, dispersion, and cytocompatibility of graphene oxides and reduced graphene oxides", Colloids and Surfaces B: Biointerfaces Volume 89, pages 1-294).

For example, modified graphene is used as a chemical or biochemical sensor for analyte molecules via selective chemical interactions. The prior art discloses rGO functionalized with poly(ethylene glycol) (PEG). Furthermore, rGO-PEG-NH$_2$ can be used to kill bacteria during an immunoassay. Thus, the detection accuracy can be increased and unwanted result noise, e.g. by bacteria growth ("Highly Sensitive Detection of DNA Hybridization on Commercialized Graphene-Coated Surface Plasmon Resonance Interface", Anal. Chem., 2014, 86 (22), pp 1 121 1-1 1216), can be avoided. On the other hand, the prior art discloses the covalent modification of antibodies or fragments thereof with PEG ("PEGylation"), with which antibodies or their fragments can be stabilized ("PEGylation of antibody fragments for half-life extension", Methods Mol. Biol. 2012; 901:233-46). In addition, PEG is used as a spacer for antibodies in an analytical medium to improve the reaction kinetics.

Functionalized graphene has also been used for the simultaneous detection of adenine and guanine by voltammetry in DNA, see Ke-Jing Huang et al. in Colloids and Surfaces B: Biointerfaces 82 (2011) 543-549.

The object of the present invention is to provide a biosensor with which an analyte molecule can be detected with particularly high sensitivity within an extremely short detection time using an electrical detection method chosen from impedance spectrometry and cyclic voltammetry.

SUMMARY OF THE INVENTION

The object is achieved by providing a biosensor having at least one working electrode covered with reduced-graphene, wherein an antibody fragment Fab or another capture molecule is covalently bound to the reduced graphene via a spacer.

The present invention particularly relates to the subject-matter according to the following items (1) to (14):

(1) A biosensor comprising the following components:
(a) a sensor base having an insulating substrate and at least one electrically conductive working electrode thereon;
(b) reduced graphene (rGO) applied to at least one of the working electrodes,
(c) spacers of different lengths covalently bound to the reduced graphene,
(d) a capture molecule covalently bound to each of the spacers.

(2) The biosensor according to (1), wherein the capture molecule is an antibody fragment Fab or an L-aptamer.

(3) The biosensor according to (1) or (2), wherein the components (b) to (d) are arranged on a working electrode, wherein the biosensor further comprises a reference electrode, or are arranged on interdigital electrodes, to which AC can be applied.

(4) The biosensor according to any preceding item (1) to (3), wherein the spacers are obtainable by reacting terminally aminated polyalkylene glycol molecules of different lengths and/or polyalkylene polyamine molecules of different lengths first with graphene and then with the capture molecule.

The spacer preferably has a hydrocarbon chain that has a chain length of preferably from 5 to 10,000 atoms and is optionally interrupted by oxygen atoms and/or amino groups.

Preferably, this spacer is attached to the rGO via amino groups; alternatively, other coupling groups are possible, which can be obtained by bonding suitable reactive groups to free carboxylic acid groups or the like existing on the graphene oxide before its reduction. In particular, the spacer is prepared by reacting at least difunctional amines, optionally of different length, such as polyethylene glycol-NH$_2$, and/or a polyalkylene amine, such as tetraethylene pentaamine, with graphene oxide and, after reduction of graphene oxide, reacting with the antibody fragment Fab or with another capture molecule obtained. In this context, the terms "derived from polyalkylene glycol-NH$_2$", "derived from polyethylene glycol-NH$_2$", "derived from polyalkylene amine" and "derived from tetraethylene pentamine" mean that a polyalkylene glycol/polyethylene glycol terminally modified with NH$_2$ groups or an oligoalkylene amine/tetraethylene pentamine was reacted with graphene and with the antibody fragment Fab or with another capture molecule, so that the resulting spacer has at least two coupling groups, wherein the reduced graphene oxide is bound to one of these groups and the antibody fragment Fab or another capture molecule is bound to the other of these groups. The bond is usually designed as —C(O)NH coupling group in each case.

The spacer preferably comprises both spacers derived from polyethylene glycol-NH$_2$ of different lengths and spacers derived from tetraethylene pentamine.

The attachment of the antibody fragment or another capture molecule to the spacer is preferably carried out by reacting a carboxyl group of the antibody fragment Fab or another capture molecule with an amino group of the spacer. This reaction produces amide groups.

Preferably, therefore, the spacer is also bound via amide groups to the reduced graphene oxide, i.e. to the graphene. This reaction can be carried out e.g. by means of a method known in the art using a carbodiimide compound as a catalyst. In one embodiment, any free functional groups of the reduced graphene oxide and/or the spacer are blocked.

This blocking is obtainable by a reaction with functional groups compounds, for example with proteins. A common composition, a so-called blocking buffer, for blocking free functional groups is milk powder/1:10PBS/0.1% Tween20.

The ready-prepared biosensor can be protected by a stabilization layer. This can for example consist of sugar. If the biosensor is used for measuring, the sugar dissolves in the measuring and rinsing liquids.

(5) A biosensor according to any one of the above items (1) to (4), wherein the covalent bond between the spacer and the capture molecule is obtained by reacting a carboxyl group of the antibody fragment Fab as the capture molecule with an amino group of the spacer or by reacting an azidoacetyl chloride-acidified amino group with a DNA molecule or RNA molecule as the capture molecule.

(6) A biosensor according to any of (1) to (5) above, which is obtainable by the steps of: (i) providing a sensor base with an insulating substrate and at least one electrically conductive working electrode located thereon, (ii) providing reduced graphene to which spacers are covalently bound, (iii) applying the graphene functionalized with reduced spacers as provided in step (ii) on the at least one working electrode, (iv) reacting a capture molecule with the product obtained in step (iii).

(7) A biosensor, which is available through the following steps: (i) providing a sensor base with an insulating substrate and at least one electrically conductive working electrode located thereon, (ii) providing reduced graphene, (iii) covalently binding spacers to the reduced graphene, (iv) applying the provided reduced graphene functionalized with spacers to the at least one working electrode, (v) reacting a capture molecule with the product obtained in step (iv), wherein the reduced graphene is dispersed in a solvent under ultrasonic treatment between steps (ii) and (iii) or between the steps (iii) and (iv).

(8) A method for producing a biosensor comprising the following steps: (i) providing a sensor base with an insulating substrate and at least one electrically conductive working electrode located thereon, (ii) providing reduced graphene which has been functionalized with difunctional amino compounds of different lengths, (iii) applying the functionalized reduced graphene provided in step (ii) to the at least one working electrode, and (iv) reacting a capture molecule with the product obtained in step (iii).

(9) A method according to (8), wherein a biosensor according to any one of claims 1 to 7 is obtained.

(10) A method of making a biosensor, comprising the steps of: (i) providing a sensor base having an insulating substrate and at least one electrically conductive working electrode thereon, (ii) providing reduced graphene, (iii) functionalizing the reduced graphene with difunctional amino compounds, (iv) applying the provided functionalized reduced graphene to the at least one working electrode and (v) reacting a capture molecule with the product obtained in step (iv), wherein the reduced graphene is dispersed in a solvent under ultrasonic treatment between steps (ii) and (iii) or between steps (iii) and (iv).

In the items (6) to (10), instead of providing reduced graphene oxide modified with spacers and its application to the working electrode, first graphene oxide may be applied to the working electrode and then the graphene oxide may be modified with the amino group-bearing precursor for the spacer, e.g. polyethylene glycol-NH$_2$ and/or tetraethylene pentamine, and then the graphene oxide is reduced (to rGO).

(11) The method according to (10), wherein the reduced graphene is applied by means of electrophoretic deposition in step (iv).

(12) The method according to (11), wherein a biosensor according to one of the items (1) to (7) is obtained.

(13) A biochip carrying a biosensor according to one of the items (1) to (7).

(14) A method for detecting an analyte, which comprises contacting an analyte present in a liquid medium with a biosensor according to any of (1) to (7) or with a biochip according to item (13) and subsequently measuring the changing of an electrical property of the biosensor effected by the interaction of the analyte with the biosensor or biochip.

Advantages of the Invention

The graphene used according to the invention is present as rGO (reduced graphene) and thus has desired unique electrical properties, above all an extremely high charge carrier mobility. This is crucial for the effect usable in the present invention. When interacting with other matter close to the rGO, this mobility is disturbed. As a result, even the smallest amounts of interacting matter results in a significant change in the electrical material properties, such as resistance. This results in the outstanding usability of graphene as sensor material for the present purposes. Reduced graphene oxide is also inexpensive to manufacture and can easily deposited on the desired target structures.

The presence of a surface spacer of variable length as described above, in particular of different length, increases the Fab mobility and thereby improves the reaction kinetics with the antigens in the analysis medium.

The spacer preferably has terminal amino groups, one of these groups is used for attachment to the rGO, the other serves for covalent bindung to the Fab. This makes it possible to bind Fab in a cheap and common way. Furthermore, this covalent bond allows for multiple use of the sensor. Fab antigen binding can be broken after the desired measurement and the biosensor can be used again. As a result, a certain recycling effect of the sensor is realized.

PEG-functionalized graphene is biocompatible and therefore easier to remove than pure rGO from a human or animal body. This is an important aspect of occupational safety and also reduces the environmental impact of the product.

Through the use of spacers of different lengths, the number of Fab fragments per unit area or volume unit can be significantly increased, so that the performance of the biosensor can be improved.

The use of Fab fragments has several advantages. They can monovalently bind to suitable antigens. In addition, non-specific binding of the antibody Fc portion is completely eliminated, since this section is no longer present when using a Fab fragment. The stability of Fab fragments that is less than that of whole antibodies is increased by binding to PEG. In addition, more Fab fragments can be accommodated on the electrode than is the case with whole antibodies.

The three-dimensional structure arrangement of graphene by homogeneous dispersion of graphene flakes and subsequent electrophoretic deposition of the structured graphene flakes have the advantage that the surface of the graphene is enlarged and thus more markers and consequently a higher sensitivity of the biosensor are made possible per unit area of the biosensor.

DETAILED DESCRIPTION OF THE INVENTION

Figure 1:
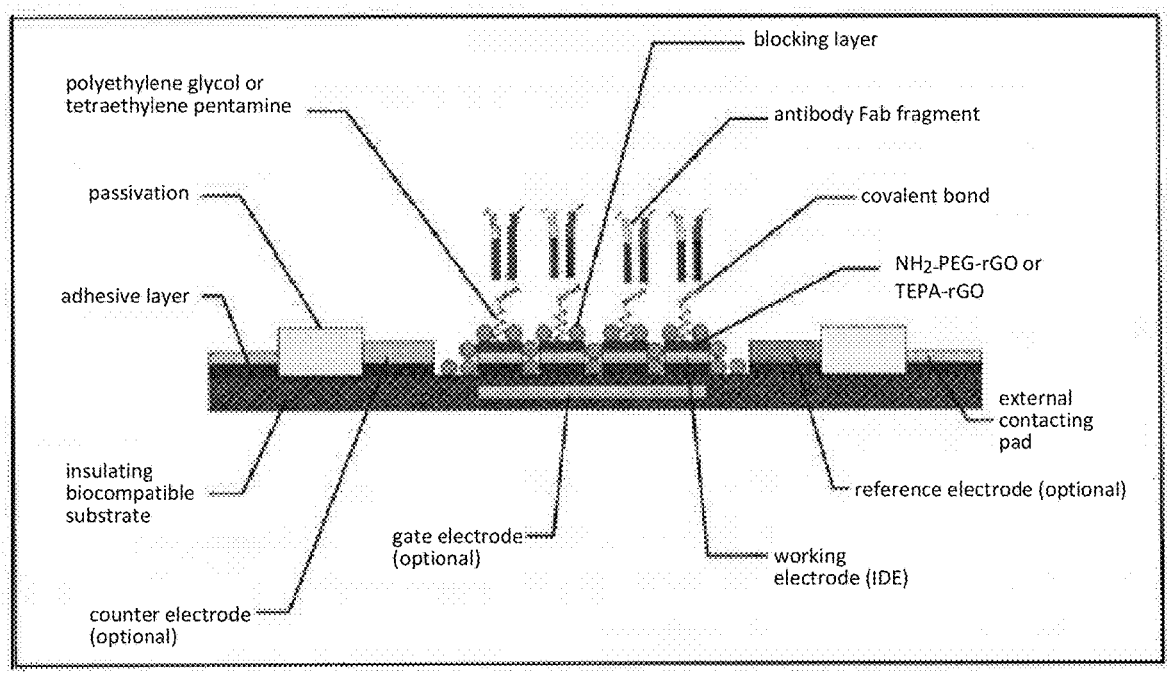
FIG. 1 shows a schematic representation of the basic structure of the biosensor or chip according to the invention having an insulating, biocompatible substrate, an adhesive layer for the electrodes, interdigital electrodes covered according to the invention, a (basically optional) counter electrode, a (basically optional) reference electrode, a (basically optional) gate electrode in the insulating substrate, a passivation (e.g. in the form of a ring) and an external terminal pad. The covalent binding of the Fab fragment is, as in all other figures below, not to be read as an —N=C=N bond but as a —C(O)NH bond.
Figure 2A:
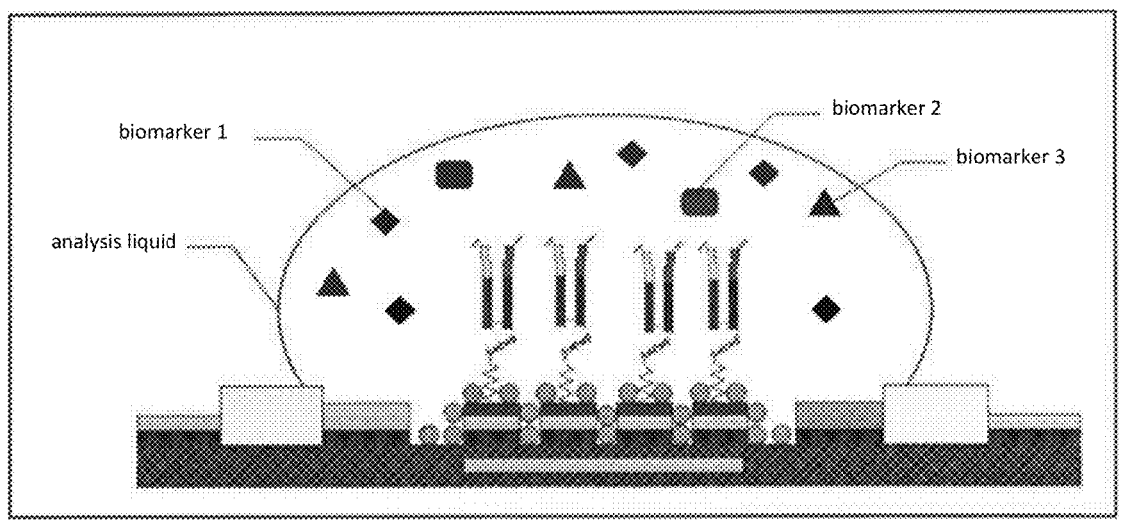
FIG. 2a shows a schematic representation of the influence of an analysis liquid.
Figure 2B:
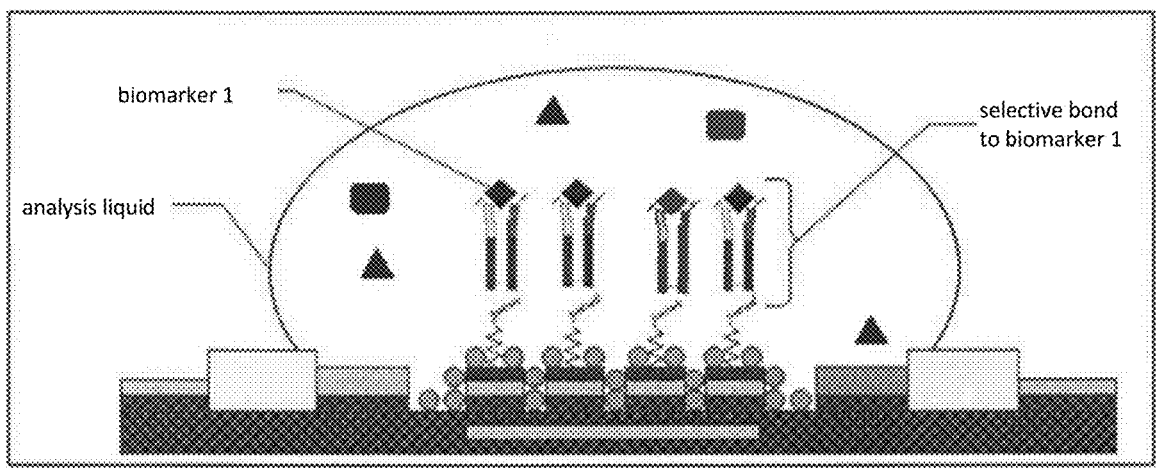
FIG. 2b shows a schematic representation of the selective biomarker binding under the analysis liquid.
Figure 3:
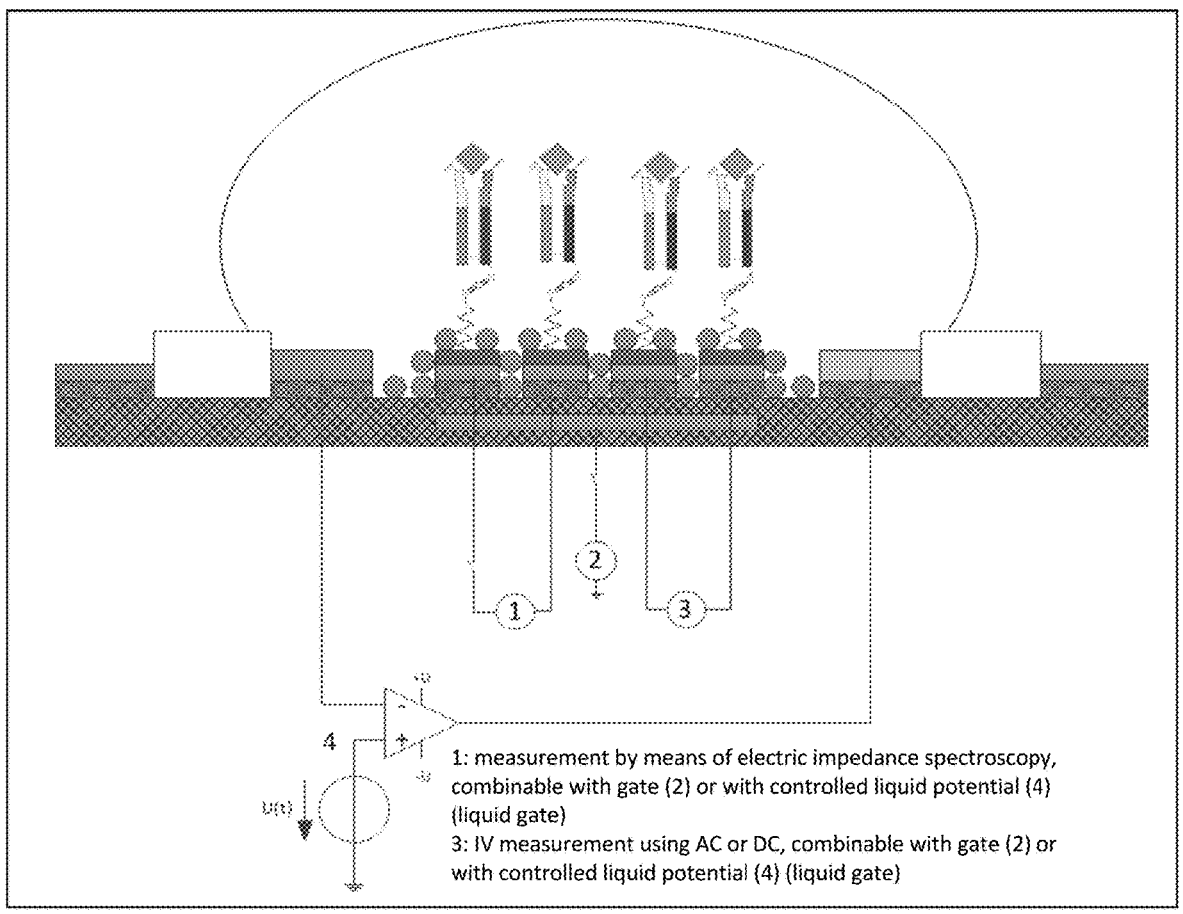
FIG. 3 shows a schematic representation of different measuring methods.
Figure 4:
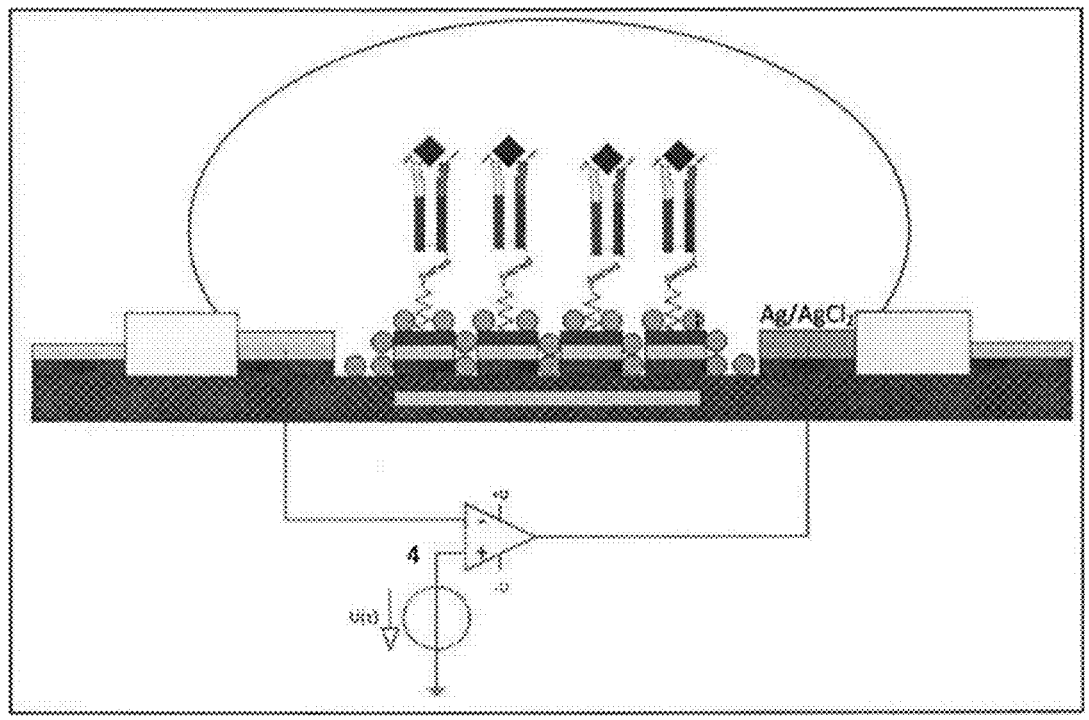
FIG. 4 shows a schematic circuit diagram using a chip level Ag/AgCl$_2$ reference electrode.

Besides the above-described embodiments (1) to (14), the present invention relates to the following embodiments [1] to [24]:

[1] A biosensor, which includes the following components: (a) a sensor base with an insulating substrate and at least one electrically conductive working electrode thereon, which is in particular formed from separately controllable interdigital electrodes, (b) reduced graphene (rGO) applied to at least one of the working electrodes, (c) a spacer covalently bound to the reduced graphene, (d) an antibody fragment Fab covalently bound to the spacer.

Preferably, spacers of different lengths are attached to the reduced graphene, with an antibody fragment Fab bound to each of these spacers. Alternatively, the antibody fragment Fab mentioned in items [1] to [24] may, quite generally, be a capture molecule as defined in this application.

[2] A biosensor according to [1], in which the components (b) to (d) are applied to interdigital electrodes, on which alternating current can be applied, wherein the impedance of the measuring system can be characterized.

[3] A biosensor according to [1], wherein the components (b) to (d) are applied to a working electrode, wherein the biosensor further comprises a reference electrode and wherein the potential of the working electrode in relation to the reference electrode is variable in defined way and the current flow between the working electrode and the reference electrode is measurable.

[4] A biosensor according to [1], wherein the components (b) to (d) are applied to interdigital electrodes, wherein the biosensor further comprises a counter electrode and optionally a reference electrode, wherein an externally applied current flow between the interdigital electrodes is detectable.

[5] A biosensor according to any one of items [1] to [4], wherein the spacer has a hydrocarbon chain having a chain length of preferably 5 to 10,000 atoms and is optionally interrupted by oxygen atoms and/or amino groups, wherein said spacer is preferably attached to the rGO via acid amide bonds.

[6] A biosensor according to any one of items [1] to [5], wherein the spacer is obtainable by reacting terminally aminated polyalkylene glycol molecules of optionally different lengths and/or polyalkylene polyamine molecules, optionally of different lengths, first with graphene and then with antibody fragment Fab.

[7] A biosensor according to any one of items [1] to [6], wherein the covalent bond between the spacer and the antibody fragment Fab is obtainable by reacting a carboxyl group of the antibody fragment Fab with an amino group of the spacer.

[8] A biosensor according to any one of items [1] to [7], wherein free functional groups of the reduced graphene and/or the spacer are blocked, preferably by means of a blocking buffer containing a protein.

[9] A biosensor according to any one of items [1] to [8], whose surfaces are coated with a protective medium soluble in an aqueous medium, e.g. a sugar layer.

[10] A biosensor according to any one of items [1] to [9], which is obtainable by the following steps: (i) the provision of a sensor base with an insulating substrate and at least one electrically conductive working electrode located thereon, which is formed, in particular, of separately controllable interdigital electrodes, (ii) providing reduced graphene to which a spacer is covalently bound, (iii) applying the spacer-functionalized reduced graphene provided according to step (ii) to the at least one working electrode, (iv) reacting an antibody fragment Fab with the product obtained in step (iii).

[11] A biosensor according to any one of items [1] to [10], comprising a plurality of working electrodes occupied with different antibody fragments Fab, each of the working electrodes having a counter electrode.

[12] A biosensor according to any one of items [1] to [11], which reacts with a change in its electrical properties to the interaction with an antigen of the antibody fragment Fab.

[13] A method for producing a biosensor comprising the following steps: (i) the provision of a sensor base with an insulating substrate and at least one electrically conductive working electrode located thereon, which is formed, in particular, of separately controllable interdigital electrodes, (ii) providing reduced graphene functionalized with at least one difunctional amino compound having an atomic chain length of 5 to 10.000 between two amino groups, wherein the difunctional amino compound is particularly selected from the group of compounds selected from polyethylene glycol-$NH_2$ of different length and tetraethylene pentaamine, (iii) applying the spacer-functionalized reduced graphene provided in step (ii) to the at least one working electrode, and (iv) reacting an antibody fragment Fab with the product obtained in step (iii).

[14] A method for producing a biosensor comprising the following steps: (i) providing a sensor base with an insulating substrate and at least one electrically conductive working electrode located thereon, which is formed, in particular, from separately controllable interdigital electrodes, (ii) producing reduced graphene functionalized with at least one difunctional amino compound having an atomic chain length of 5 to 10,000 between two amino groups, said difunctional amino compound being selected, in particular, from the group of compounds consisting of polyethylene glycol $NH_2$ of different length and tetraethylene pentamine, (iii) applying the functionalized reduced graphene obtained in step (ii) to the sensor base, preferably in the presence of at least one divalent biocompatible cation, (iv) removing the solvent, if any, and (iv) reacting an antibody fragment Fab with the product obtained in step (iii).

[15] A biochip carrying a biosensor according to one of the items [1] to [12] and having at least one component selected from a gate electrode located in the substrate, contact structures for contacting the working electrode and optionally the counterelectrode and/or the reference electrode, an insulating cover, an evaluation circuit, a channel and/or a pump for the flow of measuring or test fluid.

[16] A method of detecting an analyte which comprises contacting an analyte present in a liquid medium with a biosensor according to any one of items [1] to [12] or with a biochip according to [15] and subsequently measuring the change of an electric property of the biosensor effected by the interaction between the analyte and the biosensor or biochip.

[17] A method according to [16], wherein the change is selected from the change of the electric current, the electric voltage, the electric capacitance, the electrical inductance, the electrical resistance and the electrical impedance.

[18] A method according to [16], wherein the biosensor has interdigital electrodes as working electrodes and wherein a defined alternating signal is applied to the interdigital electrodes and the output signal is measured to characterize the impedance (Z) of the measuring system, wherein the measurement result is compared with a measurement result obtained with one comparable liquid medium in which there was no analyte.

[19] A method according to [16], wherein the biosensor has a reference electrode and the liquid medium contains a redox additive which is cyclically oxidized and reduced during the measurement by voltammetry, whereby the potential of the working electrode is changed in relation to the reference electrode, wherein the flow rate during the redox cycles is measured, the measurement result is compared with a measurement result obtained with a comparable liquid medium in which there was no analyte.

[20] A method according to [16], wherein the biosensor has a reference electrode and the liquid medium is ion conducting, wherein a potential cycle is effected via cyclic voltammetry via the reference electrode and current flowing between the working electrode and the counter-electrode is measured, wherein the measurement result is compared with a measurement result obtained with a comparable liquid medium in which there was no analyte.

[21] A method according to [20], wherein the reference electrode is provided with an operational amplifier (OPV) which compares the potential of the counter electrode and the reference electrode with a desired potential and counteracts them in case of deviations, whereby a potentiostatic construction is achieved.

[22] A method according to [16], wherein the biosensor has interdigital electrodes as working electrodes and a gate electrode is embedded in the substrate of the biosensor and this electrode is driven at a predetermined potential, thereby adjusting the working point of the graphene, wherein the current flow or the voltage between the interdigital electrodes is measured during measurement, wherein the measurement result is compared with a measurement result obtained with a comparable liquid medium in which there was no analyte.

[23] The method according to [16], wherein the biosensor has interdigital electrodes as working electrodes and a measurement is made under no-load voltage and a first of the interdigital electrodes is defined as a zero potential, the time course of the potential difference of this interdigital electrode to the second of the interdigital electrodes is detected thereby determining since when the system is in a stable state, wherein the measurement result is compared with a measurement result obtained with a comparable liquid medium in which there was no analyte.

[24] The method of any of [16] to [23], wherein the biosensor has a plurality of working electrodes covered with different antibody fragments Fabs.

The term "capture molecule" used in the present invention generally refers to a substance that can noncovalently bind another substance. This bond is preferably selective. Examples of capture molecules are antibodies, in particular Fab fragments, and aptamers, in particular from DNA and/or RNA. L-aptamers are preferred. Other conceivable interactions using a component as capture molecule are receptor-ligand interactions or specifically the biotin-streptavidin interaction. The capture molecules mentioned in this application can consist of a molecular species, i.e. of proteins, in particular Fab fragments, or aptamers. However, the capture molecules may also refer to a mixture of different such species of molecules. The remarks relating to antibody fragments Fab in the present description also apply correspondingly to other capture molecules.

As used herein, the term "analyte" or "biomarker" includes any compound or substance that can be an antigen of an antibody or a substrate of another capture molecule. The invention can be used for example for determination of pathogens, metabolites and other medically important biomarkers in the blood, saliva, rectal excretions and other body fluids in humans and animals; for monitoring drinking water and waste water; for quality control in the food industry; or in pharmacy and drug development or in safety technology for the detection of chemical or biological hazardous substances.

The term "rGO" used in the present invention denotes the product obtainable by oxidation and subsequent reduction of graphene, that is, reduced graphene oxide. The terms "reduced graphene oxide" and "reduced graphene" are used interchangeably herein.

The term "antibody fragment Fab" used in the present invention refers to the Fab fragment of an antibody (immunoglobulin), for example, IgG. A term used synonymously herein is "Fab fragment" or "Fab" for short. The term "Fab" is used for both individual molecules and for the genus, as is common in the designation of chemical compounds.

The biosensor according to the invention is preferably an on-chip biosensor which can detect extremely low concentrations of defined biomarkers in liquids.

The sensor base is a substrate with biocompatible surface, such as glass, biocompatible polymers, $Si_3N_4$, various silicon oxides, e.g. amorphous or epitaxial $SiO_2$ or other suitable materials.

The substrate itself can be insulating, a semiconductor such as silicon, or even electrically conductive, provided it is suitably insulated on its surface.

Figure 7:
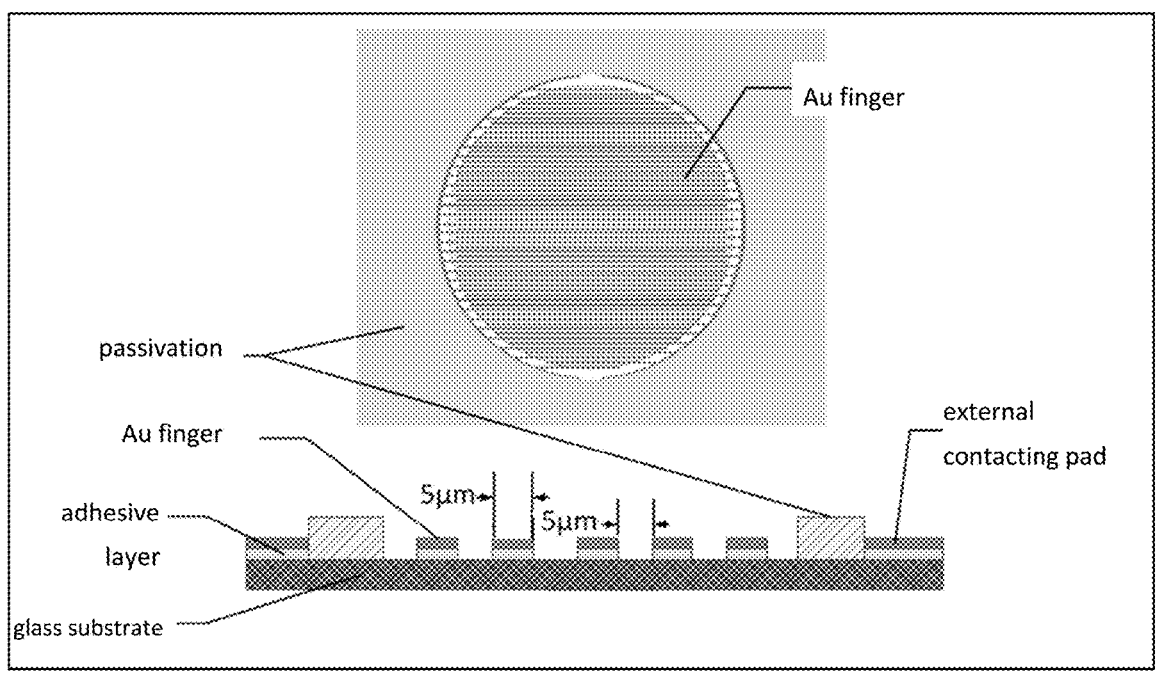
FIG. 7 shows the schematic representation of an IDE finger structure.

The biosensor according to the invention has a base with an insulating substrate, to which at least one working electrode is applied. Each of these working electrodes may be a single surface electrode or interdigital electrodes (IDEs) (FIG. 7). Other electrodes are optional. If interdigital electrodes are switched as positive and negative electrodes, for example, a further electrode can be used as a reference electrode. If only one working electrode used, it is connected against a counter electrode; a reference electrode can also be used in this variant to monitor the working electrode or the counter electrode. In a particular embodiment, which can be combined with all the above embodiments, a (substrate) gate electrode is used. This can be produced by typical semiconductor processes known to those skilled in the art, such as thin-film techniques, thick-film techniques or ion implantation. The reference electrode may be an Ag/AgCl electrode printed as a paste on the surface of the sensor. If interdigital electrodes are used, both electrode structures may be, but need not be, completely coated with the modified rGO, even if only one of them is to serve as a working electrode and the other is to serve as a pseudo-reference electrode, as described below.

On the substrate, first a structured adhesion layer can be applied, on which the metallic electrode structures adhere particularly well, for example a Ti layer. Then, the metal of the working electrode(s), for example aluminum, platinum, gold or another noble metal or other electrically conductive material known to a skilled person, is applied on it. The structured plane of the electrodes can equally be used for external connection pads of a chip, such as shown in FIGS. 1 to 4. A passivation layer, for example of a plastic material such as SUB, may be arranged e.g. in the form of a frame around the electrodes in order to protect any exposed electrical conductors against the measuring liquid and at the same time to form a recess for them.

All electrodes can be integrated on the chip level.

FIG. 7 shows the schematic representation of an IDE finger structure (interdigital structure).

Figure 8:
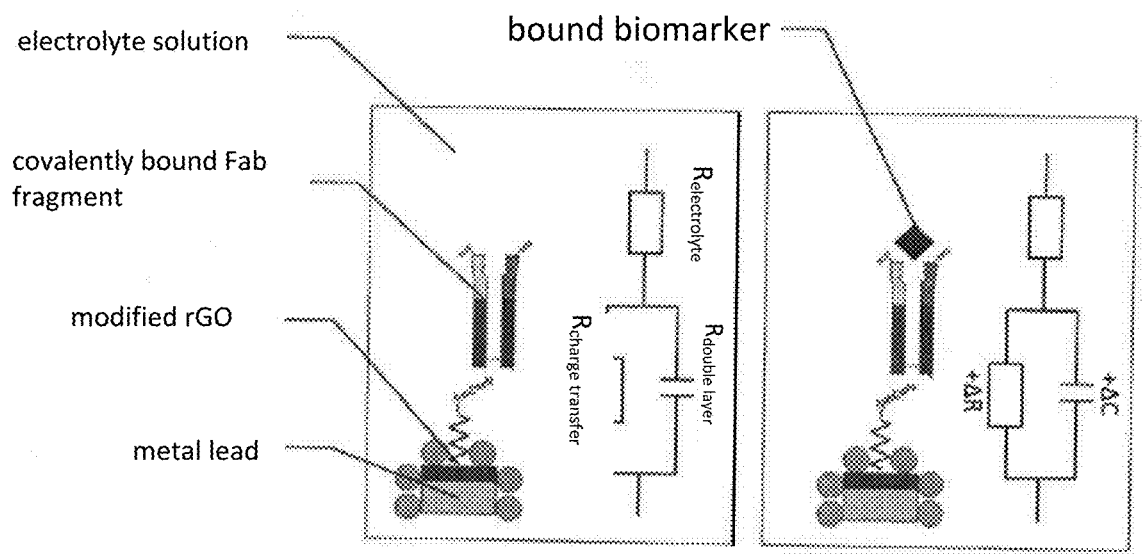
FIG. 8 shows a simplified electrical equivalent circuit diagram of an IDE finger, with and without analyte ("biomarker") binding in electrolyte solution.

FIG. 8 shows a simplified electrical equivalent circuit diagram of an IDE finger, with and without biomarker binding in electrolyte solution.

In principle, the distances of the IDE finger structure should be <5 μm (FIG. 7). It is known that the sensor sensitivity increases exponentially with reduced finger distances.

The miniaturized $Ag/AgCl_2$ reference electrode can be integrated at the chip level (FIG. 4); it is preferably printed as mentioned.

Figure 6:
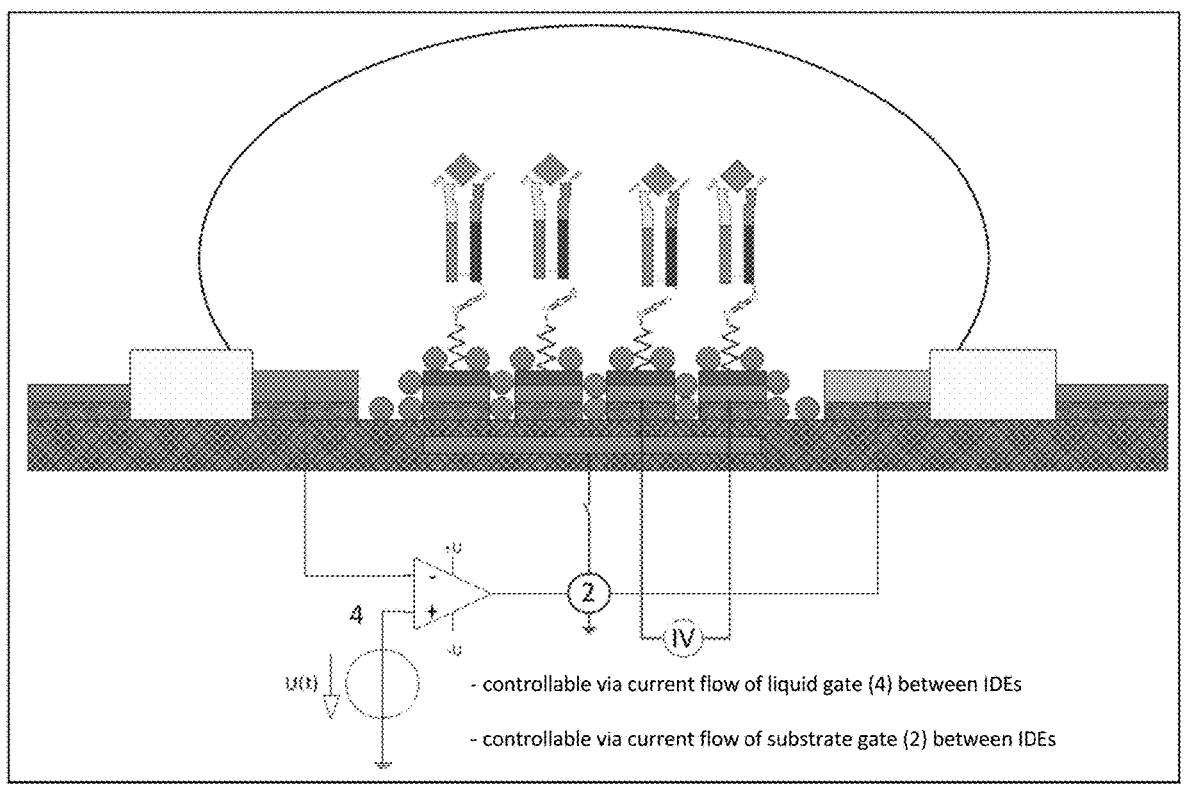
FIG. 6 shows a schematic design of a graphene biosensor FET which can be controlled via a substrate gate or via a liquid gate (conductive detection liquid).

The biosensor according to the invention can be constructed using gate electrodes (substrate gate and/or liquid gate, FIGS. 3 and 6) as FET (field-effect transistor), which leads to higher sensitivity and to the possibility of signal adaptation. The substrate gate electrode is isolated in the carrier (its electrical drive is not shown in the figures); when activated by an electrical potential, it influences the electronic structure of the rGO. The term "liquid gate" means that a defined electrical potential can be adjusted by means of counter electrode and reference electrode in the electrolyte; the current flow between the IDEs can thus be controlled.

In the biosensor according to the invention, the sensor base is preferably formed by a structure with an interdigital electrode (IDE) as a working electrode on a substrate (FIG. 1).

There is graphene on the working electrode or the interdigital electrodes. Preferably, the entire electrode surfaces(s) of the working electrode(s) is/are occupied therewith.

Production of Reduced Graphene (Oxide)

Basically, graphene is produced by two main methods. On the one hand by means of CVD (Chemical Vapor Deposition), wherein a graphene layer from the gas phase (e.g. from $CH_4$) is deposited catalytically on e.g. copper or nickel. This way of production is very cost-intensive, since among other things usually a transfer step, which transfers the catalytically deposited graphene to the actual desired structure, is needed here. However, the graphene that can be generated in this way is very defect-free and has perfect electrical properties. The disadvantage, however, is that it is difficult to attach functional groups to this graphene, because there are hardly any structural defects as a linker for such groups. One can artificially effect structural defects (e.g. by a plasma treatment) to then bind desired functional group to the graphene surface. However, this deteriorates the electrical properties which are special for this production variant.

According to the other method, graphene is produced by chemical and/or mechanical exfoliation of graphite. The big advantage over the CVD graphene is the comparatively cost-effective production as well as the possible mass production. Graphite can be easily understood as a column of stacked graphene layers. In most cases, the modified HUMMERS method is used for the exfoliation of the graphite, whereby the graphite is strongly oxidized by means of chemical solution. As a result, hydroxyl and epoxy groups are formed in the intermediate layer of the graphite, which is why the individual layers remove farther from each other and the layer structure loses stability. Furthermore, hydroxyl, carbonyl and carboxyl groups are formed at the layer edges. The surface is thus highly hydrophilic. When a strong polar solvent is added, it settles around the individual functional surface groups. The individual layers exfoliate and a suspension of GO (graphene oxide) is formed. The exfoliation can still be optimized by applying ultrasound. The structural defects can now be used to bind defined functional groups to the surface. Preferably, at this stage, the graphene is modified with the spacer, in particular by binding an amino-containing compound to COOH groups present on the graphene surface. However, since the electrical properties of the graphene are rather moderate after the "consumption" of a part of the COOH groups by the high number of defects, a subsequent chemical or thermal reduction of the groups formed by the oxidation can be used to return to an almost perfect lattice, as is the case here. This changes the material designation classically into rGO (for reduced graphene oxide), and rGO has similarly good electrical properties as CVD graphene. Due to the chemical and mechanical exfoliation, the reduced graphene is typically deformed and also folded.

Furthermore, as mentioned, CVD graphene is deposited on a work surface and can only be transferred to a target structure by some transfer steps. On the other hand, rGO often occurs after production as a "powder" consisting of rGO flakes, which can be brought in suspension to apply them directly to the desired structure.

Typically, rGO is prepared by the method described above. Different functionalization steps during production lead to the changed surface structures that can then be used selectively. However, other methods are also included in the invention.

Application of Reduced Graphene Oxide to the Working Electrode(s)

The electrophoretic deposition of rGO offers the possibility of depositing rGO on the working electrode or electrodes in a cheap, simple and focused manner.

Before the rGO is electrophoretically deposited, it is added with preferably biocompatible cations, in particular 2-valent cations such as $Mg^{2+}$ according to the invention. These are adsorbed by the graphene and/or can also intercalate. As a result, the surface potential of the individual graphene flakes, also referred to as zeta potential, is increased. This surface potential makes electrophoretic deposition possible. After deposition, the concentrated accumulation of the stored cations with corresponding counterions forms a layered substance, e.g. $Mg(OH)_2$ in the case of use of $Mg^{2+}$ ions which react with $OH^-$ ions. These come from the (aqueous or water-containing) solvent or separately added water. This layer is very strong and adhesive and therefore serves at the same time as an adhesive layer/adhesion promoter between graphene and the electrode surface. Furthermore, other additives may be added, for example cellulose, an (inorganic, organic or inorganic-organic) polymer or rubber or a mixture of several such additives in order to additionally increase the adhesion.

The simple application of graphene to the target structure by means of electrophoretic deposition offers a very cheap and easy method of production.

Figure 13:
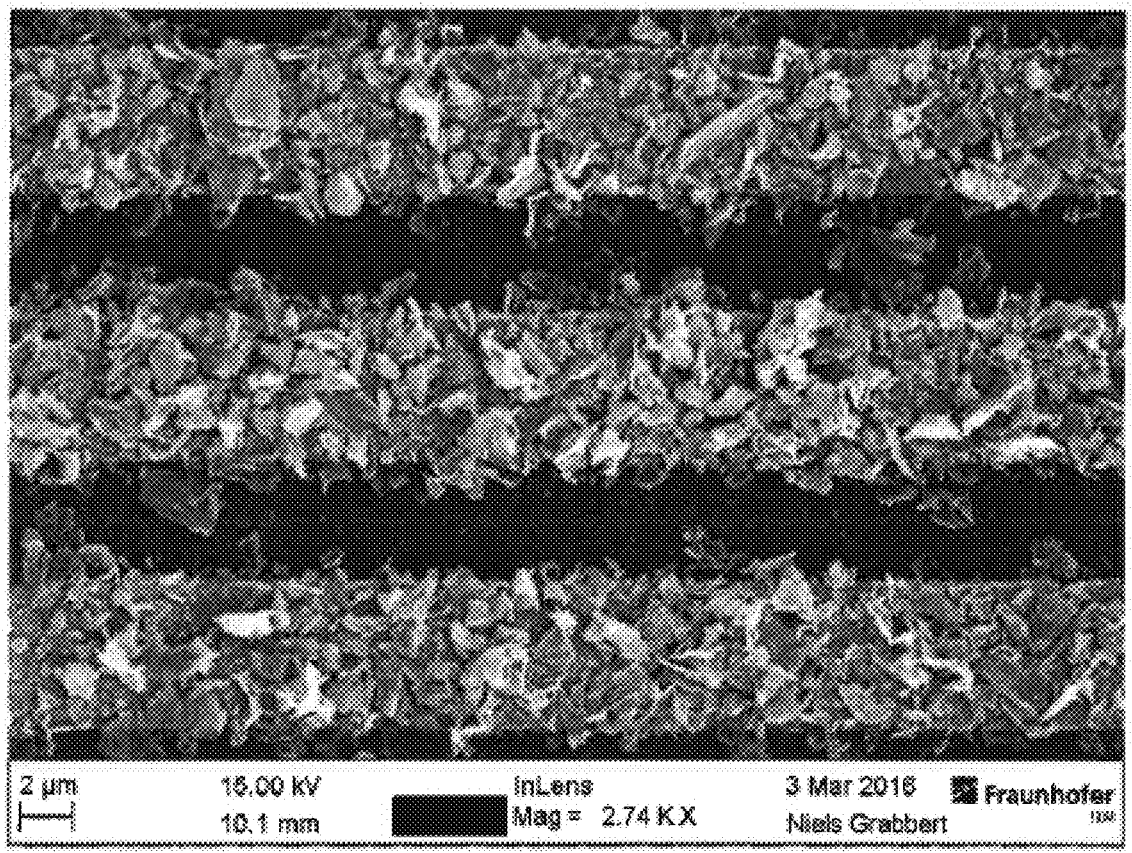
FIG. 13 shows an SEM image of a graphene-deposited IDE.

FIG. 13 shows a SEM image of a graphene deposited IDE. You can see a dense population with a variety of flakes. As a result, the surface of the electrodes is greatly increased. After electrophoretic deposition, graphene flakes adhere statistically distributed on the electrode surface. As a result of this orientation, the active sensor surface made of rGO is extremely enlarged, as can also be seen from FIG. 13. To further increase the sensitivity, Fabs are bound to it instead of the larger antibody during the further process steps. The above-mentioned unique electrical properties of graphene combined with this double increase in sensitivity lead to a unique sensitivity of the possible measurement methods.

The rGO may be modified with the spacer(s) before or after the application on the sensor base. Preferably, the modification is prior to application. The rGOs used in the present invention are prepared by reacting with the functionalized spacers. In this case, preference is given to using $NH_2$—PEG-$NH_2$ and/or TEPA, as described above.

In one embodiment of the invention, the surface of the graphene may be significantly increased by electrophoretic deposition of folded graphene flakes by carrying out step (a) and/or step (b) in the following manner.

a) Graphene flakes (rGO) are dispersed in a preferably organic solvent. The dispersion is preferably carried out by ultrasonic treatment, for example by sonotrode. In this way, aggregated rGO flakes are dissolved or separated and then homogeneously dispersed. The rGO flakes are deformed or folded by the intense acoustic waves, resulting in a three-dimensional structure of the two-dimensional rGO flakes. The graphene flakes preferably have a size (maximum length) of 0.1 to 10.0 µm, more preferably 0.2 to 3.0 µm.

(b) The folded rGO flakes are subsequently deposited on the working electrode. This is preferably done by electrophoretic deposition (EPD). The folded rGO flakes are characterized by a significant increase in their surface area. The surface enlargement significantly increases the sensitivity of the biosensor.

By the manufacturing method using the step (a) and/or the step (b), there is available a biosensor which, without these steps, has a much smaller number of capture molecules per unit area of the working electrode and/or can bind a significantly lower number of biomarkers per unit area of the working electrode. A preferred factor for increasing the number of captured capture molecules and/or the number of biomarkers that can be bound is at least 1.2, more preferably at least 1.5, even more preferably at least 2.0, even more preferably at least 3.0, and most preferably at least 5.0. This factor can be determined by performing the same procedure once with and once without step (a) and/or step (b) and determining the number of capture molecules and/or biomarkers per unit area. This number or of the difference factor can be determined via the detectable function or property of the capture molecules and/or biomarkers. That is, for example, a detectable property, e.g. fluorescence, of the biomarker is measured once with and once without performing step (a) and/or step (b) and the measured ratio of values is assumed as the factor mentioned above.

On the product, i.e. on the produced biosensor, this production method can be detected by SEM examination of the graphene layer. In the inventive three-dimensional structuring of graphene, at least part of the planar graphene flakes is not located in the plane of the surface on which the graphene flakes have been deposited. Rather, the areas of these graphene flakes occupy every possible angle to the plane of said surface. This portion of the graphene flakes is preferably at least 10%, more preferably at least 30% and even more preferably at least 50% of the total graphene flakes.

In a particularly preferred embodiment, by the three-dimensional structuring of the graphene flakes the number of capture molecules and/or the biomarkers per unit area of the working electrode is higher than the theoretically possible number in a two-dimensional structuring. In a still more preferred embodiment, the number is by a factor of at least 1.1, 1.2, 1.5, 2.0 or 3.0 higher than the theoretically possible number in a two-dimensional structuring. Again, this number or the difference factor can be determined via the detectable function or property of the capture molecules and/or biomarkers.

Ultrasonic treatment deforms the graphene flakes, i.e. the flake structure is no longer a flat plane. It is preferred that the proportion of these deformed flakes in the total number of flakes on a working electrode, as determined by SEM analysis, be at least 10%, 20%, 30%, 50% or 70%.

Figure 17:
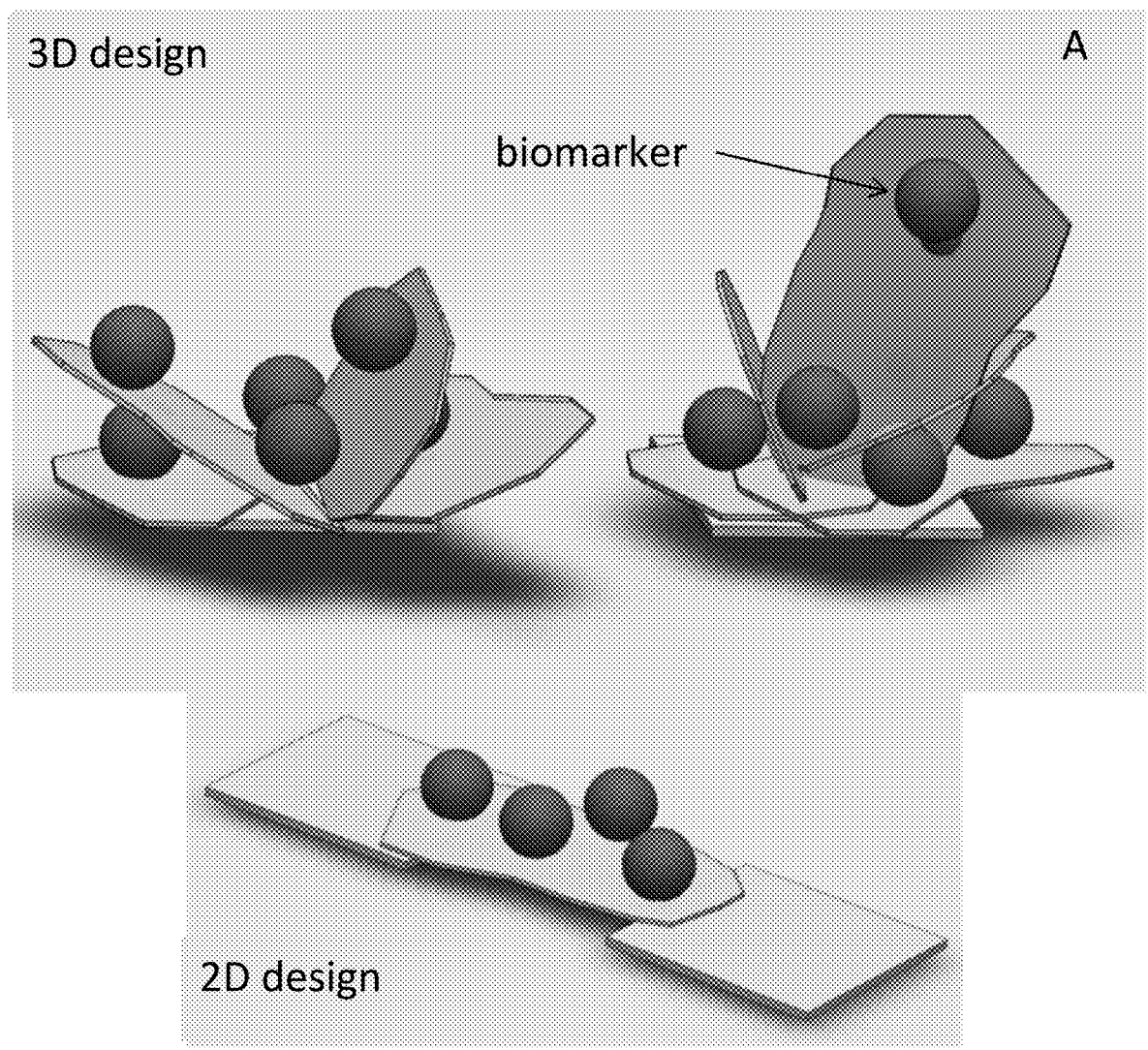
FIG. 17 shows schematically the increase of the surface by generation of three-dimensional structures of two-dimensional rGO flakes.

FIG. 17 shows schematically the increase of the surface by generation of three-dimensional structures of two-dimensional rGO flakes.

Figure 18:
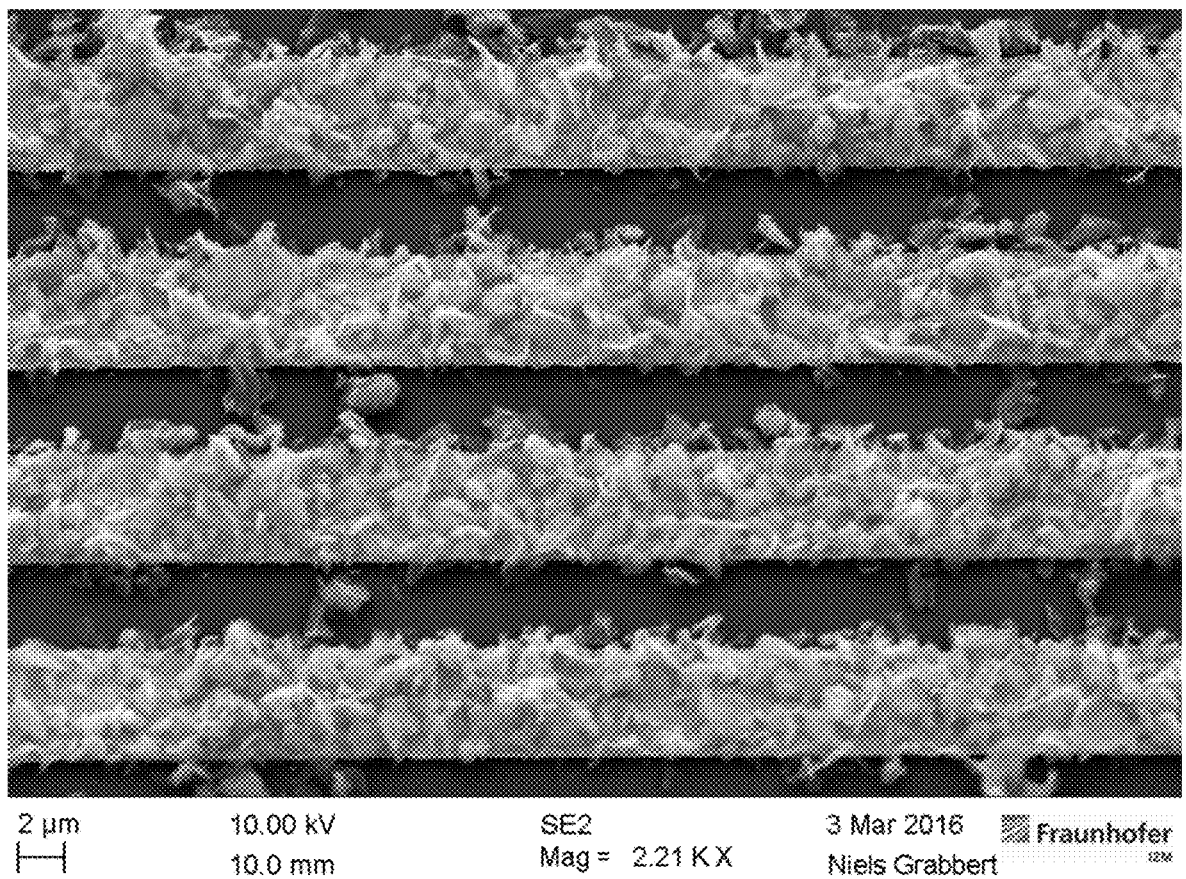
FIG. 18 shows a SEM image of three-dimensional graphene flakes.

FIG. 18 shows a SEM image of three-dimensional graphene flakes.

Attachment of the Fab Fragments or Other Capture Molecules

The free amino end of the functionalization of the PEG-$NH_2$ or TEPA is suitable for attaching to the Fab. However, it is also possible to use a COOH residue as functionalization on the rGO. This is because antibodies can also be attached to rGO-COOH groups via covalent bonds. Because Fab fragments are essentially composed of amino acids, they have both free —COOH and free —NH$_2$ groups. Therefore, both carboxy and amine residues on the rGO are possible as a binding terminal to the Fab to form an amide bond. However, preference is given to free —NH$_2$ groups. Because with the use of Ig (immunoglobulins) and Fab fragments produced therefrom, N-termini (NH$_2$ residues) are located at the antigen binding site of the light and heavy chain. The opposite side of the antigen binding site ends with C-termini (COOH residue). To bind the Fab to the rGO with the correct orientation, the rGO should therefore be functionalized with —NH$_2$. Thus, the complementary COOH group of the Fab fragment can bind to the rGO and ensure the correct orientation.

The combination of the use of rGO and the described functionalization has the advantage that the spacer-functionalized rGO, e.g. NH$_2$—PEG-rGO or TEPA-rGO, can be used as bioelectrical interface with high biocompatibility of NH$_2$-PEG-rGO and TEPA-rGO.

As already stated above, for example, tetraethylene pentamine (TEPA) of formula (1) H$_2$N—CH$_2$CH$_2$—NH—CH2CH2—NH—CH$_2$CH$_2$—NH—CH$_2$CH$_2$—NH$_2$ (Formula (1)) can be used for the functionalization. Commercially available TEPA is often a mixture of several compounds (oligomers) which are derived from a different monomer number and therefore have a different chain length. The TEPA used in the present invention can therefore contain e.g. one or more of the compounds selected from the group consisting of N-(2-aminoethyl)-N'-{2-{2-aminoethyl) amino}ethyl}-1,2-ethane diamine; 4-(2-aminoethyl)-N-(2-aminoethyl)-N'-{2-{(2-aminoethyl)amino}ethyl}-1,2-ethanediamine; 1-(2-aminoethyl)-4-[(2-aminoethyl)amino] ethyl]piperazine) and 1-[2-[[2-[(2-aminoethyl)amino]ethyl] amino]ethyl]piperazine). These compounds differ in their structure and thus their reactivity with the reactants, namely reduced graphene on the one hand and antibody fragment Fab or another capture molecule on the other hand.

Thus, the term "tetraethylene pentamine" or "TEPA" as used herein includes not only the compound of the formula (1) but also any of the other compounds mentioned above alone or in a mixture of two or more of these compounds.

The polyethylene glycol-NH$_2$ (PEG-NH$_2$) used in the present invention is derived from polyethylene glycol (PEG). PEG is a polymer of ethylene glycol monomer units and can have a wide variety of chain lengths. Typical chain lengths of commercially available PEG include 200, 400, 600 or 1500 monomer units. In the present invention, the PEG-NH$_2$ may consist of 5 to about 3500, preferably 10 to 600, more preferably 20 to 100 of the monomer units. PEG-NH$_2$ of a single chain length or PEG-NH$_2$ of different chain lengths can be used. That is, the present invention also includes an embodiment in which a mixture of PEG-NH$_2$ of different chain lengths is used for producing the biosensors. In addition, this mixture may also contain one or more of the above-mentioned various TEPAs.

In this way, spacers of different lengths and also reactivity on the reduced graphene of a biosensor can be obtained. The use of spacers of various lengths has the advantage that the sensory surface can be increased. Specifically, this means that the antibody fragments Fab or other capture molecules can be present quasi in several layers on the reduced graphene and can nevertheless be easily accessible.

In one embodiment of the present invention, the NH$_2$-rGO termini can be acidified using azidoacetyl chloride.

Through this functionalization, click chemistry can be used as a binding mechanism between rGO and capture molecule. The most diverse molecules can be bound to the rGO surface using click chemistry. This can be done without the addition of additional reaction chemistry. For example, L-aptamers can be successfully linked as an antibody equivalent to rGO in this way. Aptamers consist of synthetically produced DNA/RNA fragments, which bind highly selectively to defined antigens due to their specific spatial organization. This binding is comparable to the binding of antibodies to antigens. The binding affinities are also comparable to antibodies. Compared to proteins (antibodies/FABs), molecules of DNA/RNA (aptamers) are much more stable to temperature and chemicals. As a result, easier integration within various manufacturing methods is possible compared to susceptible antibodies.

L-aptamers are a special genus of aptamers. They are characterized by a left-handed chirality. As a result, an enormously increased biostability is achieved because DNA/RNA polymerases are no longer able to break down the DNA/RNA portions of the aptamers.

The use of fully synthetic capture molecules also allows the avoidance of animal models and at the same time allows an increased quality of the aptamers compared to antibodies.

Figure 19:
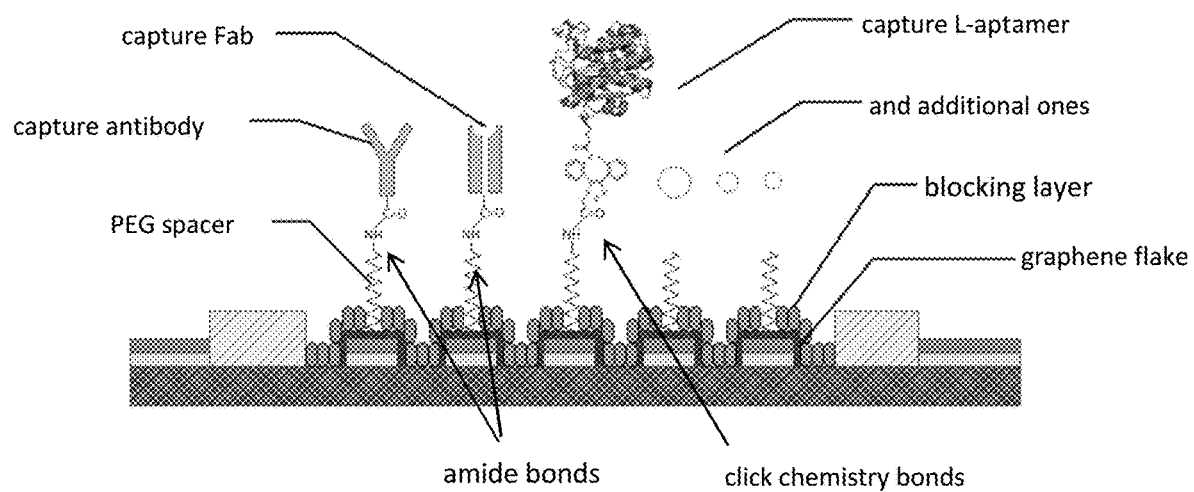
FIG. 19 is a schematic representation of the functionalization by means of click chemistry and amide bond.

FIG. 19 is a schematic representation of the functionalization by means of click chemistry and amide bond.

The combination of click chemistry and amide bond to functionalization may be advantageous, for example to produce different selectivities on a sensor. In a particularly advantageous manner, the production of a three-dimensional structural arrangement described above can be combined with the functionalization by means of click chemistry and/or amide bond.

Antibody Fragments Fab

A particular advantage of the invention is the use of antibody fragments Fab instead of whole antibodies, since Fab fragments are smaller, linear or elongated and do not have the Y-form of antibodies.

By combining the use of Fab fragments and spacers having different lengths, not only the number of Fab fragments per unit area, but also the number of Fab fragments per unit height can be increased. Thereby, the number of Fab fragments per unit volume can be drastically increased.

The biosensor according to the invention uses only the sensitive part of an antibody. Thus, in comparison to the use of the entire antibody, a better weight and volume ratio between Fab fragment and biomarker can be realized. Calculations show that the effective radius of an antibody is 5, while that of the Fab fragment is 1.25. Assuming a circle, this gives an area of the antibody of 78 nm$^2$ and the Fab fragment of 4.91 nm$^2$. Since an antibody on this surface has two binding sites, the ratio of binding sites per unit area is eight times higher for a Fab fragment than for an antibody.

As an example, the binding of the antigen procalcitonin (PCT) to IgG antibody on the one hand and Fab fragment on the other hand can be considered. The mass of an IgG antibody is 150 kDa, the mass of a Fab fragment is 46 kDa. The mass of procalcitonin (PCT) is 13 kDa. Binding of PCT to an antibody results in a mass ratio (2×PCT)/antibody of 17.3%, while binding of PCT to a Fab fragment results in a mass ratio of PCT/Fab of 28.2%. Thus, the use of a Fab fragment allows the binding of a much higher number of antigens per mass employed. The better weight and volume ratio leads to higher sensitivity of the biosensor. The small area of the Fab fragment compared to the area of the whole antibody allows more sensitive material per unit area to be applied.

Production of the Biosensor on a Chip

In the following, by means of a preferred embodiment, the production of the biosensors according to the invention is described at the chip level. However, it should be clear that all steps are possible in other combinations. In a first step, conventional sensor techniques, such as thin or thick film technology, are used to create a sensor body consisting of a nonconductive substrate onto which at least one working electrode, usually made of a suitable biocompatible metal, is deposited. One or more suitable intermediate layers such as an adhesive layer may be arranged between the substrate and the working electrode(s). The plane of the working electrode(s) can also be used to form contacts; alternatively, the contacts may be buried in the substrate.

In addition to the working electrode(s), a counter electrode may be formed, which may also be arranged on the same plane as the working electrode(s) and contacted in a suitable manner.

If a substrate gate electrode is to be present, then it is formed in the insulating substrate and contacted by known methods.

If a reference electrode is to be present, it can be printed at a suitable location, for example on the substrate or an adhesive layer, for example as Ag/AgCl paste. Contact structures located on the substrate that lead to the electrodes can be covered with an insulating material, for example a plastic. This can be applied so that the working electrodes come to lie in recesses of this material, such that a liquid to be detected remains in place as a drop or the like and does not flow away.

Figure 5:
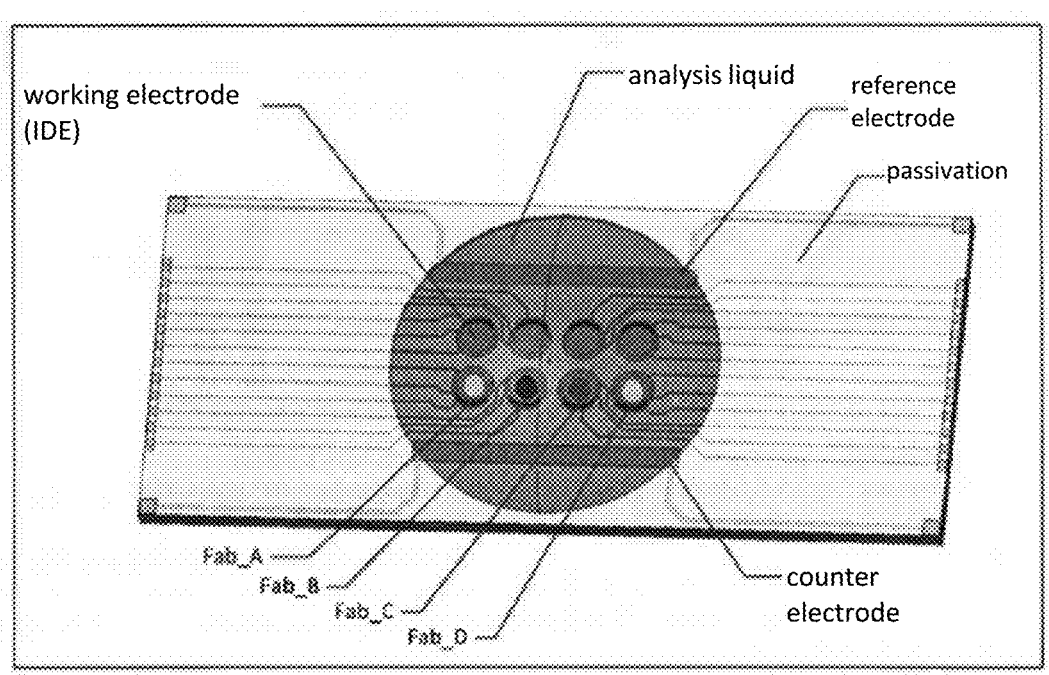
FIG. 5 shows a schematic representation of a multiplex detection by using four different Fab fragments on four IDE structures, one working electrode per IDE structure and one reference electrode on a single biochip.

The working electrodes, preferably interdigital electrodes, are coated with reduced graphene oxide (rGO), which has been functionalized with a suitable spacer as described above, e.g. with aminated polyethylene glycol ($NH_2$-PEG-rGO) and/or tetraethylene pentamine (TEPA-rGO). Before the coating, the graphene, before or after the functionalization with the spacer, is preferably charged with 2-valent biocompatible metal cations, in particular with $Mg^{2+}$ ions, which thereby intercalate and form an adhesive layer in the form of the hydroxide when applied to the electrodes. Subsequently, defined antibody Fab fragments or other capture molecules are covalently bound to the amino groups of the spacers on the reduced graphene oxide. The Fab fragment determines the selectivity to a specific analyte ("biomarker") and can be adapted accordingly to the desired analyte or biomarker. An arrangement of several interdigital electrodes on a chip is possible. These may have the same or different Fab fragment functionalization (FIG. 5).

After functionalization, a blocking layer can be deposited to eliminate free active surfaces. At the same time, this layer reduces the parasitic interaction by saturating the free bonds on the surfaces and suppressing non-specific biomarker binding.

An additional stabilizing layer may be applied to improve the lifetime and reliability of the biosensor. This can for example consist of sugar, which dissolves again when using the biosensor.

The covalent binding between graphene and antibody Fab fragment allows a higher mobility of the Fab fragment compared to adsorbed Fab fragments. This ensures a better application of barrier layers (blocking layer) without affecting the Fab fragments. This blockage leads to a reduction of parasitic interactions. In addition, the strong covalent bond between graphene and Fab fragments resists purification processes, allowing multiple use of the sensor.

Figure 14:
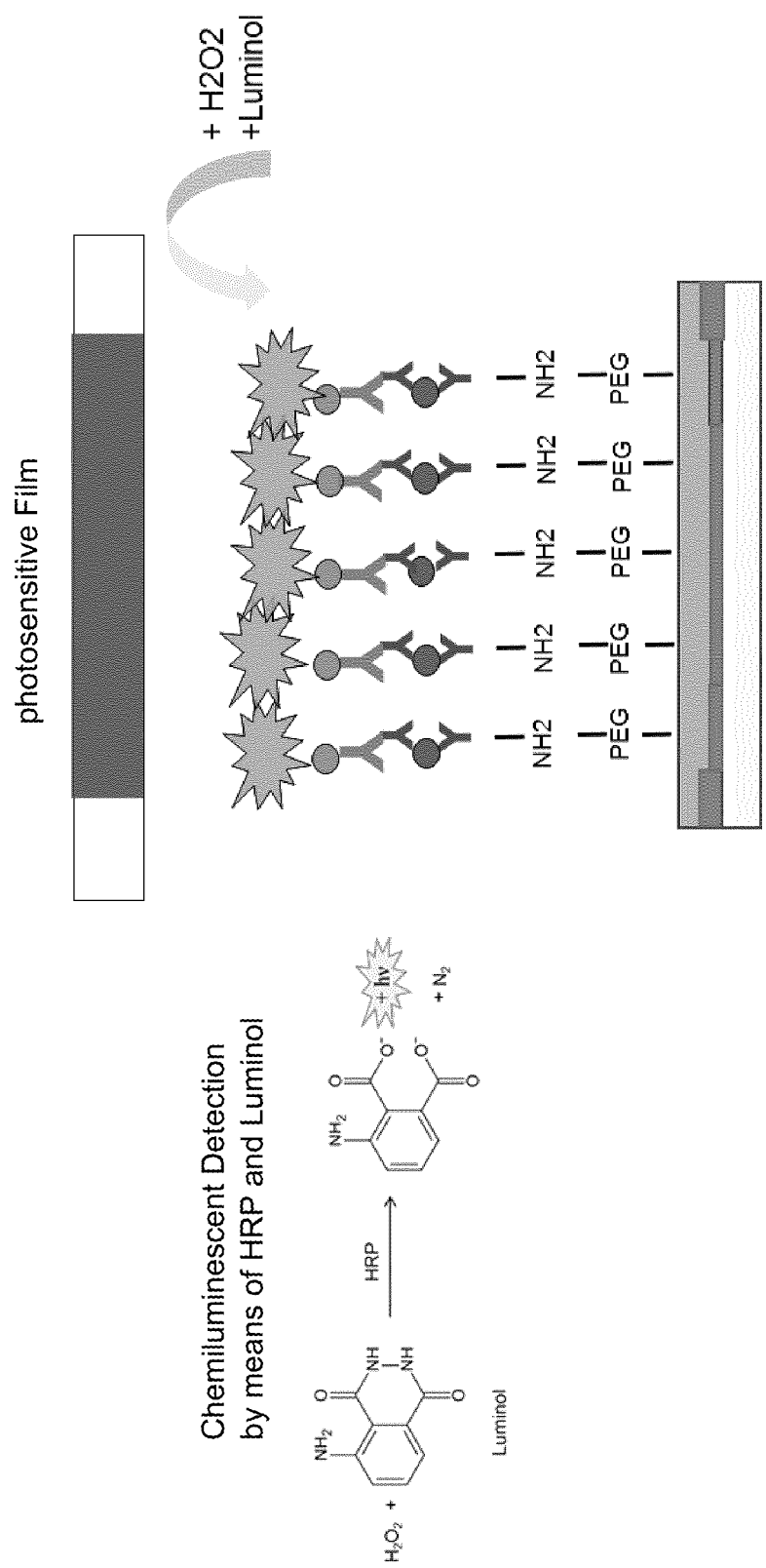
FIG. 14 shows the schematic representation of chemiluminescence detection by means of sandwich ELISA.
Figure 15:
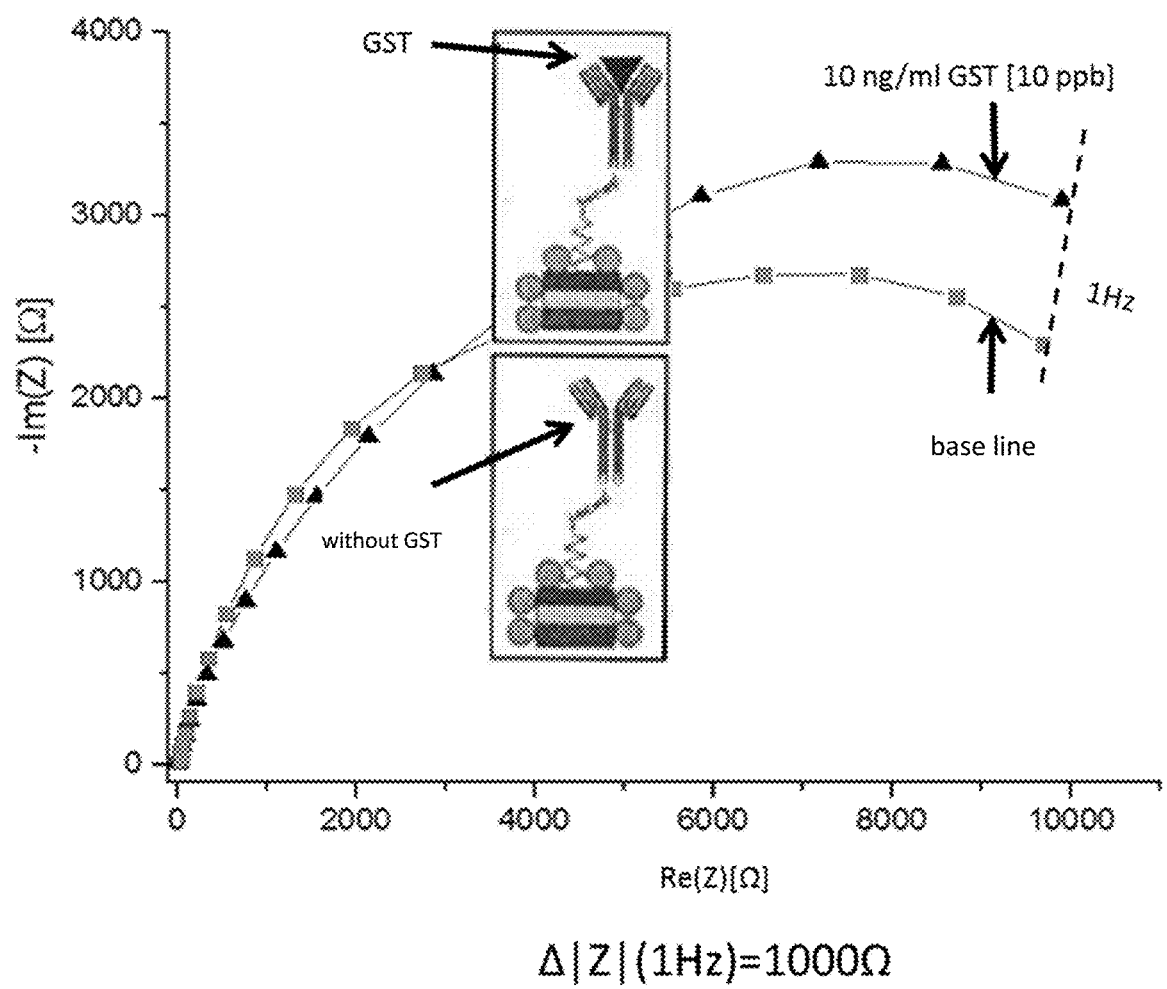
FIG. 15 shows an impedance spectrum with and without GST as analyte (biomarker). The detection of 10 ng/ml GST in the measuring electrolyte could be shown. This resulted in a difference of impedance without and with biomarker by a significant 1000 ohms.

In the present case, for the sake of simplicity the covalent binding to the graphene was detected not with a Fab fragment but with an antibody (IgG anti-GST, polyclonal). The binding between antibody and graphene could be detected by chemiluminescence detection. Here, GST (glutathione 5-transferase) was used as a biomarker, which was detected by sandwich ELISA (FIGS. 14 and 15).

Measurement of Biomarker Binding

The biosensor detects the various levels of biomarkers via the change in its electrical properties. A change in the biomarker concentration (FIGS. 2a and 2b) produces at least one measurable change, which is selected from the group consisting of a measurable change in the electrical current, the electrical voltage, the electrical capacitance, the electrical inductance electrical resistance and the electrical impedance of the biosensor.

Examples

The present invention will be further illustrated by the following example. A biosensor is prepared by the following steps (1) to (5):

(1) Preparation of a Working Electrode Structure

One or more IDE electrode structures are deposited on a nonconductive substrate of gold or other suitable metal using standard semiconductor technology.

(2) Production of an Electrophoretically Separable r GO-PEG-$NH_2$ Suspension by Ultrasound First, rGO-PEG-$NH_2$ is added to a dielectric solvent (e.g. ethanol, isopropanol, acetone, NMP (N-polymethyl pyrrolidone), dimethylformamide (DMF)) at a concentration of several mg/ml. The mixture is sonicated several times by sonotrode. Thereafter, the surface of the rGO-PEG-$NH_2$ is charged with cations by the addition of $MgCl_2 \cdot 6H_2O$ ($Mg^{2+}$ is adsorbed to rGO-PEG-$NH_2$ and/or intercalated into the structure). If necessary, PVDF, PE, PMMA or other polymers or inorganic and/or other organic substances may be added as adhesion promoters. The solution is dispersed for several hours by means of sonotrode ("ultrasonic mixer"). The resulting dispersion is centrifuged at >2000 rpm and the supernatant is separated from sediments. The supernatant is filtered by means of a syringe filter (<10 μm).

(3) Electrophoretic Deposition of rGO-PEG-$NH_2$ on the Working Electrode

A gold IDE is used as the working electrode (negative potential). An inert counter electrode (positive potential) is used. Both electrodes are immersed in the already prepared rGO-PEG-$NH_2$ solution; layer growth is varied over the applied voltage, deposition time, electrode spacing and area, as well as different rGO-PEG-$NH_2$ and $MgCl_2 \cdot 6H_2O$ concentrations of the solution; the deposition occurs either in DC mode or in positive pulsed voltage mode; $Mg^{2+}$ ions attached to the rGO form the compound $Mg(OH)_2$ after some time with $OH^-$ ions present in the system. A matrix of graphene-$Mg(OH)_2$ could be detected by means of SEM and EDX (FIG. 13).

(4) Hardening

For this purpose, the chip is placed in a vacuum oven after deposition and baked for several hours. The solvent residues are thus pulled out of the surface and the layer is densified. $Mg(OH)_2$ forms a solid adherent layer with rGO-PEG-$NH_2$ and the electrode surface. If desired, this layer can be optimized by adhesion promoters referred to herein.

(5) Binding of Fab Fragments to rGO-PEG-NH$_2$

Fab fragments are dispersed in 1:10 PBS (phosphate buffered saline). NHS (N-hydroxysuccinimide) and EDC (1-ethyl-3-[3-dimethylaminopropyl]carbodiimide) are also dissolved in 1:10 PBS. Portions of the NHS/EDC solution are added to the Fab fragments which react with each other at room temperature for several minutes. The reacted solution is then pipetted onto the rGO-PEG-NH$_2$ surface of the chip. There, the activated Fab fragments form stable covalent compounds with the rGO-PEG-NH$_2$. The batch is washed from the chip surface by means of 1:10 PBS. Thereafter, a blocking buffer (e.g. from milk powder/1:10 PBS/0.1% Tween20) was added to the sensor surface and incubated for some time. Excess and unbound blocking buffer is purified using wash buffer (e.g. with 1:10 PBS or 1:10 PBS/0.1% Tween20).

(6) Electrical Measuring Methods

All measurements are made in a test or analyte solution to which an electrolyte salt is added.

a. Electrochemical impedance spectroscopy

In this case, a defined alternating signal is applied to the interdigital electrodes in the measuring system and the output signal is measured in order to characterize the impedance (Z) of the measuring system. The impedance is often monitored in the frequency range Z (w).

Figure 9:
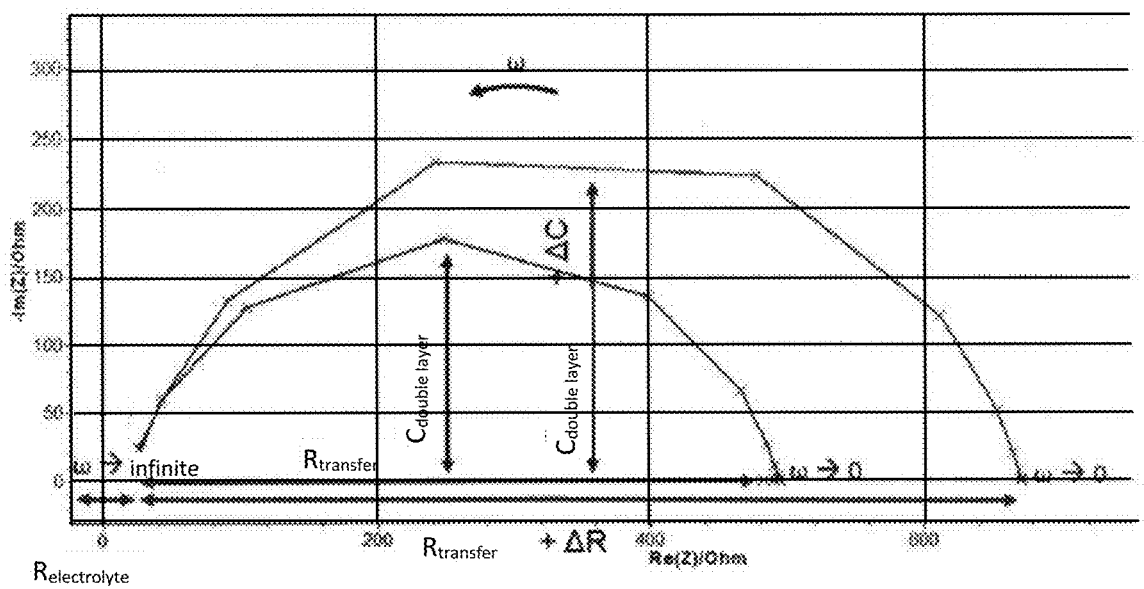
FIG. 9 shows the schematic change of the impedance as a function of the presence of a biomarker and at different angular frequencies w, shown in the complex number plane.

To simplify the characterization of the system, Z (w) is plotted in the complex plane. It is then possible to extract the individual electrical components from the plot and to easily recognize changes. FIGS. 8 and 9 show a simplified electrical equivalent circuit diagram of an IDE finger without (FIG. 8) and with (FIG. 9) biomarker binding in electrolytic solution.

b. Cyclic voltammetry (CV)

During the CV measurement, it is favorable to integrate a redox additive in the measurement solution (e.g. K$_3$Fe(CN)$_6$/K$_4$Fe(CN)$_6$), if the electrode surface does not itself form a redox system.

During the measurement with the aid of cyclic voltammetry, the added redox system is cyclically oxidized and reduced. This will change the potential of the working electrode in relation to a reference electrode in a defined way. At the same time the flow is measured. Redox reactions that are triggered by these potential cycles are clearly recognizable by increased current flow later. Since the current flow depends on the surface of the electrode and this electrode surface changes upon the attachment of antigens to the antibodies (the charge transfer from one electrode to the other and vice versa is thereby changed), the attachment of the antigens can be detected because the CV image differs from the CV image in the absence of antigens.

There are two options for the measurement strategy.

1. There is only one Fab working electrode. In the case of the presence of interdigital electrodes, these are set to the same potential and form the working electrode, which are measured in an electrolyte against a reference electrode (e.g. Ag/AgCl$_2$). The reference electrode can be integrated on chip level using Ag/AgCl$_2$ paste pressure.

2. Alternatively, one of the interdigital electrodes may serve as a pseudo-reference and the other as a working electrode.

c. Liquid "Gate" CV

Figure 10:
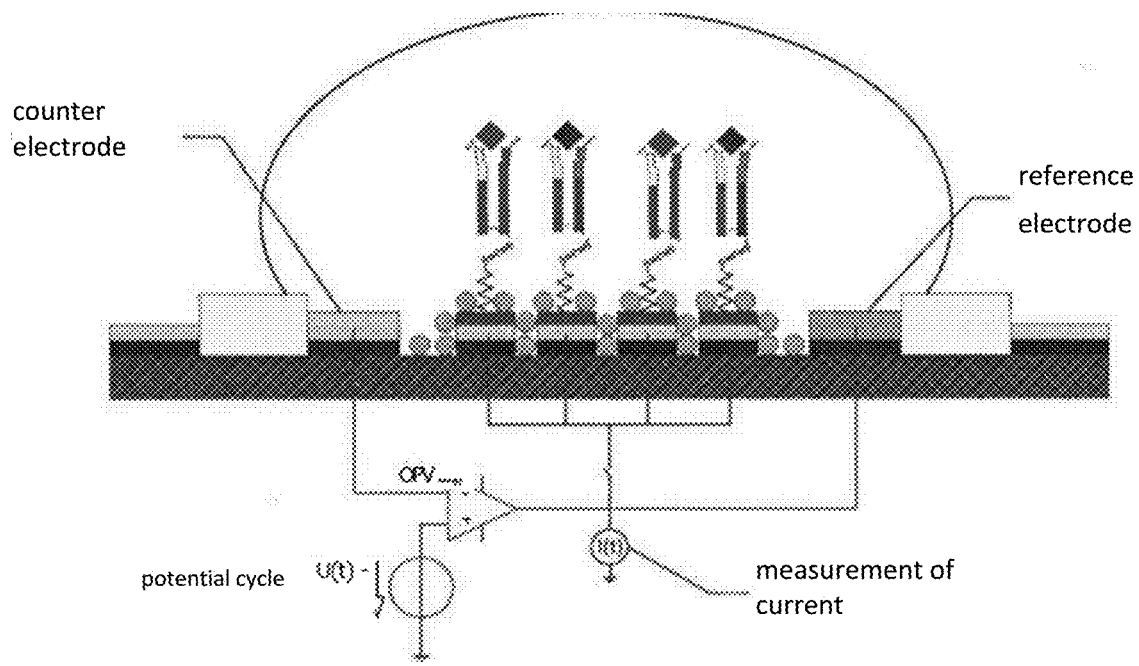
FIG. 10 shows the schematic representation of the measurement using an operational amplifier (OPV) and a counter electrode.
Figure 11:
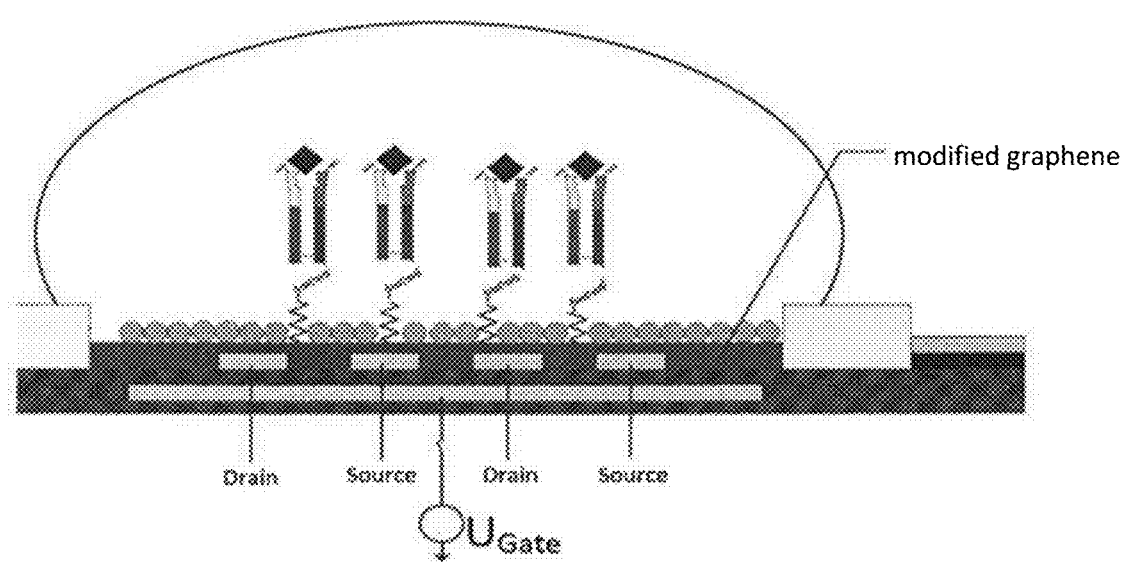
FIG. 11 shows the schematic representation of the adjustment of the operating point of the graphene over $U_{Gate}$. The IDEs can be used as the drain and source here; alternatively, the IDEs are set to a potential and measured against the counter or working electrode. Then, either the current flow or the voltage is measured between drain and source.
Figure 12:
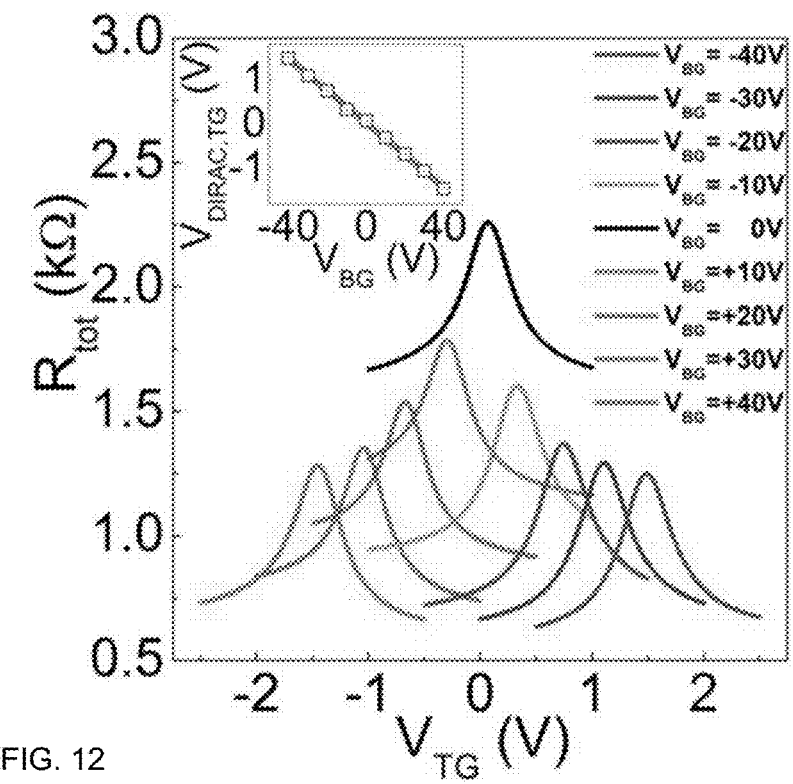
FIG. 12 shows the change in resistance (working point shift) at different gate voltages (VTG). The resistance change is determined from the IV measurement (measurement of current flow or voltage).

In this method, the test liquid serves as an electrolyte. Again, it is beneficial to integrate a redox additive in the measurement solution (e.g. K$_3$Fe(CN)$_6$/K$_4$Fe(CN)$_6$), if the electrode surface does not itself form a redox system. The CV-typical potential cycle (via the electrolytes) is effected into the system via the reference electrode, and the currents which have flowed are measured via the electrodes (Fabs-coated electrode(s) against the counter electrode or the reference electrode). As described above, the effected potential is also plotted against the current flow. This results in a similar redox characteristic as in the method b. In order to keep the potential in the liquid at the desired level (despite triggered redox reactions), the reference electrode can be equipped with a operational amplifier (OPV) and a counter electrode. The OPV compares the potential of the counter electrode and the reference electrode with the desired potential (potential cycle) and controls in the event of deviations (FIG. 10). In this case, a potentiostatic construction is achieved as known from the prior art.

d. Operating point setting or Sensitivity improvement by means of gate arrangement It is possible to utilize the semiconducting properties of the graphene in such a way that the system operating point can be adjusted thereby resulting in a higher sensitivity. For this purpose, a gate electrode can be embedded in the substrate, which can be driven with a certain potential. As can be seen from FIG. 11, the operating point of the graphene can be adjusted via $U_{Gate}$. The current or voltage is measured between the interdigital electrodes (referred to herein as "drain" and "source").

Figure 16:
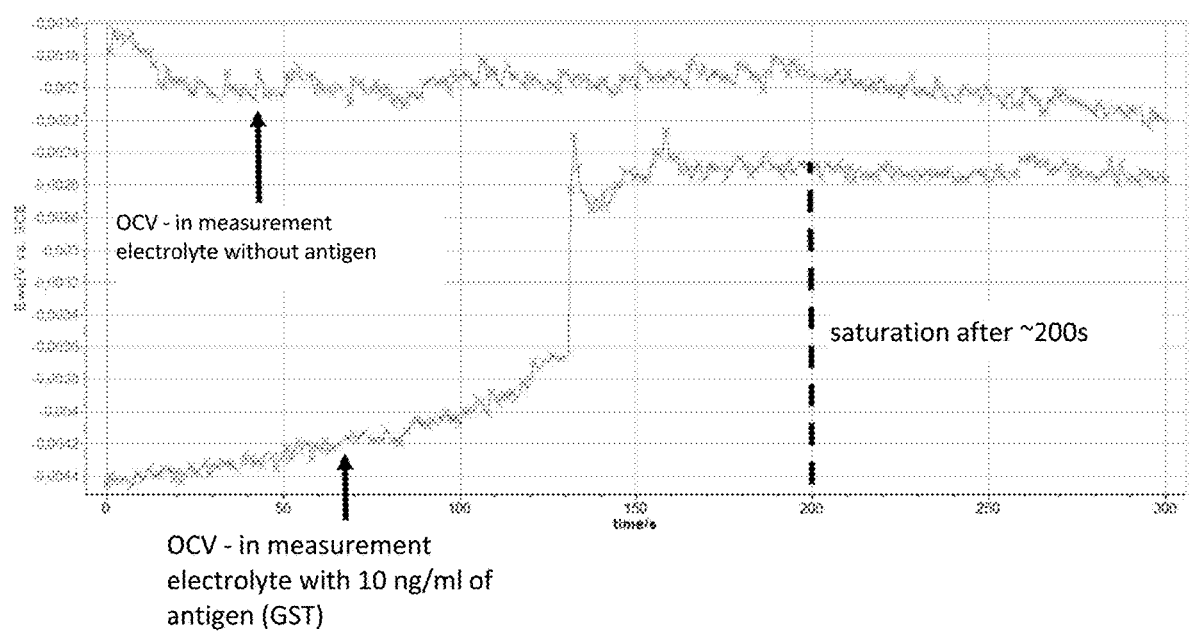
FIG. 16 shows the reaction kinetics of the biosensor with and without 10 ng/ml GST in the measuring electrolyte. It was possible to detect a detection time of about 200 s.

In addition, OCV measurement, i.e. a measurement under open-circuit voltage is performed. In this case, a first electrode path (one of the interdigital electrodes coated by Fabs) is defined as a zero potential and the potential difference to the other electrode path is determined. This can be used to estimate when the system is in a stable state. If the OCV remains stable, there will be no change in the surface of the electrodes or no chemical (or significantly less) interaction between the electrolytes and electrode. As a result, the reaction kinetics of the detected biomarker (analyte, antigen) can be visualized with the surface, since a mass transport and change of the surface occurs here. When the surface is saturated, the OCV stabilizes and the biosensor can be measured. At the same time, the speed of the sensor can be determined at the same time. FIG. 16 shows the OCV of a prototype.

The invention claimed is:

1. A biosensor, comprising:
   (a) a sensor base having an insulating substrate and at least one electrically conductive working electrode disposed on said insulating substrate;
   (b) reduced graphene applied to at least one said working electrode;
   (c) a plurality of spacers having mutually different lengths covalently bound to said reduced graphene; and
   (d) a capture molecule covalently bound to each of said spacers.

2. The biosensor according to claim 1, wherein said capture molecule is an antibody fragment Fab or an L-aptamer.

3. The biosensor according to claim 1, wherein components (b) to (d) are arranged on said working electrode, and wherein at least one of:
   the biosensor further comprises a reference electrode, or said working electrode is formed of interdigital electrodes to which alternating current can be applied.

4. The biosensor according to claim 1, wherein said spacers are formed by reacting terminally aminated polyalkylene glycol molecules having different lengths and/or polyalkylene polyamine molecules having different lengths first with said graphene and then with said capture molecule.

5. The biosensor according to claim 1, wherein a covalent bond between said spacer and said capture molecule is formed by reacting a carboxyl group of an antibody fragment Fab as said capture molecule with an amino group of a spacer of said plurality of spacers or by reacting an azidoacetyl chloride-acidified amino group with a DNA or RNA molecule as said capture molecule.

6. The biosensor according to claim 1, obtained by the following process steps:
    providing a sensor base having an insulating substrate and at least one electrically conductive working electrode arranged thereon;
    providing reduced graphene to which spacers are covalently bound;
    applying the spacer-functionalized reduced graphene to the at least one working electrode; and
    reacting a capture molecule with the product obtained in the applying step.

7. A biochip, comprising a chip carrying a biosensor according to claim 1.

8. A method of detecting an analyte, the method comprising:
    contacting an analyte present in a liquid medium with a biosensor according to claim 1 or with a biochip according to claim 7 and subsequently measuring a change of an electrical property of the biosensor effected by an interaction of the analyte with the biosensor or biochip.

9. A biosensor obtained by the following process steps:
    providing a sensor base having an insulating substrate and at least one electrically conductive working electrode arranged thereon;
    providing reduced graphene;
    covalently binding spacers to the reduced graphene to form a spacer-functionalized reduced graphene;
    applying the spacer-functionalized reduced graphene to the at least one working electrode;
    wherein the reduced graphene is dispersed in a solvent under ultrasonic treatment between the step of providing reduced graphene and the covalently binding step or between the covalently binding step and the applying step; and
    reacting a capture molecule with the product obtained in the applying step.

10. A method of producing a biosensor, the method comprising the following steps:
    providing a sensor base having an insulating substrate and at least one electrically conductive working electrode disposed on said sensor base;
    providing reduced graphene functionalized with difunctional amino compounds of different lengths to form functionalized reduced graphene;
    applying the functionalized reduced graphene to the at least one working electrode; and
    reacting a capture molecule with the product obtained in the applying step.

11. The method according to claim 10, wherein the biosensor produced, comprises:
    (a) a sensor base having an insulating substrate and at least one electrically conductive working electrode disposed on said insulating substrate;
    (b) reduced graphene applied to at least one said working electrode;
    (c) a plurality of spacers having mutually different lengths covalently bound to said reduced graphene; and
    (d) a capture molecule covalently bound to each of said spacers.

12. A method of producing a biosensor, the method comprising the following steps:
    providing a sensor base having an insulating substrate and at least one electrically conductive working electrode disposed on said insulating substrate;
    providing reduced graphene;
    functionalizing the reduced graphene with difunctional amino compounds to form functionalized reduced graphene;
    applying the functionalized reduced graphene to the at least one working electrode;
    dispersing the reduced graphene in a solvent under ultrasonic treatment between the step of providing reduced graphene and the functionalizing step or between the functionalizing step and the applying step; and
    reacting a capture molecule with the product obtained in the applying step.

13. The method according to claim 12, wherein the applying step comprises applying the reduced graphene by electrophoretic deposition.

14. The method according to claim 13, wherein the biosensor produced, comprises:
    (a) a sensor base having an insulating substrate and at least one electrically conductive working electrode disposed on said insulating substrate;
    (b) reduced graphene applied to at least one said working electrode;
    (c) a plurality of spacers having mutually different lengths covalently bound to said reduced graphene; and
    (d) a capture molecule covalently bound to each of said spacers.

* * * * *

UNITED STATES PATENT AND TRADEMARK OFFICE
CERTIFICATE OF CORRECTION

PATENT NO. : 10,989,684 B2
APPLICATION NO. : 16/301104
DATED : November 13, 2018
INVENTOR(S) : Niels Grabbert et al.

It is certified that error appears in the above-identified patent and that said Letters Patent is hereby corrected as shown below:

In the Specification

Column 17, Lines 25-28 should read as follows:
The impedance is often monitored in the frequency range $Z(\omega)$.
To simplify the characterization of the system, $Z(\omega)$ is plotted in the complex plane.

Signed and Sealed this
Second Day of August, 2022

Katherine Kelly Vidal
*Director of the United States Patent and Trademark Office*